US009574206B2

(12) United States Patent
Koprowski et al.

(10) Patent No.: US 9,574,206 B2
(45) Date of Patent: *Feb. 21, 2017

(54) ENGINEERED BIOMASS WITH INCREASED OIL PRODUCTION

(71) Applicants: Biotechnology Foundation, Inc., Ardmore, PA (US); Thomas Jefferson University, Philadelphia, PA (US)

(72) Inventors: Hilary Koprowski, Wynnewood, PA (US); Vyacheslav Andrianov, Warrington, PA (US); Mykola Borysyuk, Somerset, NJ (US)

(73) Assignees: Biotechnology Foundation, Inc., Ardmore, PA (US); Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/451,826

(22) Filed: Aug. 5, 2014

(65) Prior Publication Data

US 2015/0067919 A1 Mar. 5, 2015

Related U.S. Application Data

(63) Continuation of application No. 12/664,875, filed as application No. PCT/US2008/066696 on Jun. 12, 2008, now Pat. No. 8,847,010.

(60) Provisional application No. 60/944,283, filed on Jun. 15, 2007.

(51) Int. Cl.
*C12N 15/82* (2006.01)
*C12N 5/14* (2006.01)

(52) U.S. Cl.
CPC ............ *C12N 15/8247* (2013.01); *C12N 5/14* (2013.01)

(58) Field of Classification Search
None
See application file for complete search history.

(56) References Cited

U.S. PATENT DOCUMENTS

| | | | |
|---|---|---|---|
| 2005/0118665 A1 | 6/2005 | Zhou et al. | |
| 2005/0193443 A1 | 9/2005 | Dale Rock et al. | |
| 2005/0204612 A1* | 9/2005 | Connemann et al. | 44/437 |
| 2006/0206961 A1 | 9/2006 | Cirpus et al. | |
| 2007/0050867 A1 | 3/2007 | Harada et al. | |
| 2007/0134201 A1 | 6/2007 | Schleper | |

FOREIGN PATENT DOCUMENTS

WO 0036114 A1 6/2000

OTHER PUBLICATIONS

Bouvier-Nave et al 2000 (European Journal of Biochemistry 267: p. 85-96).*
International Search Report for International Application No. PCT/US08/066696 dated Jan. 8, 2009.
Sebastien Baud, et al, An integrated overview of seed development in Arabidopsis thaliana ecotype WS, Plant Physiol. Biochem, 40 (2002) 151-160.
Ramli, et al, Control analysis of lipid biosynthesis in tissue cultures, from oil crops shows that flux control is shared between fatty acid synthesis and lipid assembly, Biochem, J. (2002) 364, 393-401.
Pierrette Bouvier-Nave, et al., Expression in yeast and tobacco of plant cDNAs enclosing acyl CoA:diacylglycerol acyltransferase, Eur. J. Biochem, 267, 85-96 (2000).
Klein, et al., Transfer of foreign genes into intact maize cells with high-velocity microprojectiles, Pro. Natl., Acad, Sci. USA, vol. 85, pp. 4305-4309, Jun. 1988.
Bao et al., "Supply of Fatty Acid is One Limiting Factor in the Accumulation of Triacylglycerol in Developing Embryos", Article, Plant Physiol. vol. 120, Aug. 1999, pp. 1057-1062.
Baud et al. "Multifunctional Acetyl-CoA Carboxylase 1 is Essential for Very Long Chain Fatty Acid Elongation and Embryo Development in Arabidopsis", Article, The Plant Journal 2003, 33, pp. 75-86.
Beisson et al., "Arabidopsis Genes Involved in Acyl Lipid Metabolism", Article, Plant Physiol. vol. 132, Jun. 2003, pp. 681-697.
Belknap et al, "pBINPLUS/ARS: an Improved Plant Transformation Vector Based on pBINPLUS", Article, BioTechniques 44:753-756, May 2008.
Boulton et al., "Specificity of Agrobacterium-Mediated Delivery of Maie Streak virus DNA to Members of the Gramineae", Article, Plant Molecular Biology 12:31-40, 1989.
Cahoon et al., Expression of a Coriander Desaturase Results in Petroselinic Acid Production in Transgenic Tobacco, Article, pro. Natl. Acad. Sci, USA vol. 89, pp. 11184-11188, Dec. 1992.
Cazzonelli et al. Characterization of a Strong, Constitutive Mung Bean (*Vigna radiata* L.) Promoter with a Complex Mode of Regulation in Planta, Article, Transgenic Research 2005, 14:941-967.
Casas et al., Transgenic Sorghum Plants via Microprojectile Bombardment, Article, Proc. Natl, Acad, Sci, USA vol. 90, pp. 11212-11216, Dec. 1993.
Denecke et al., Plant and Mammalian Sorting Signals for Protein Retention in the Endoplasmic reticulum Contain a Conserved Epitope, Article, Embo Journal, vol. 11, No. 6 pp. 2345-2355, 1992.
D'Halluin et al., "Transgenic Maize Plants by Tissue Electroporation", Article, The Plant Cell, vol. 4, 1495-1505, Amer. Soc. Plant Physiol, Dec. 1992.
Foster et al., "A Tobacco Cryptic Constitutive Promoter, tCUP, revealed by T-DNA Tagging", Plant Molecular Bilogy, 41:45-55 pp. 45-55, 1999.
Fromm et al. "Expression of Genes Transferred into Monocot and Dicot Plant Cells by Electroporation", Article, Proc. Natl. Aca. Sci, USA 82:5824-5828, Sep. 1985.
Gao et al., Agrobacterium Tumefaciens-Mediated Sorghum Transformation using a Mannose Selection System, Article, Plant Biotech Jml. 3:591-599, 2005.

(Continued)

*Primary Examiner* — Matthew Keogh
(74) *Attorney, Agent, or Firm* — NK Patent Law, PLLC

(57) ABSTRACT

The present invention relates to a genetically modified plant having an increased amount of oil in its green biomass as compared to the oil in the green biomass of its non-genetically modified counterpart. The plants may be used for producing bio-fuels such as biodiesel fuel.

12 Claims, 6 Drawing Sheets

(56) References Cited

OTHER PUBLICATIONS

Giannelos et al., "Tobacco Seed Oil as an Alternative Diesel Fuel: Physical and Chemical properties", Article, Industrial Crops and products Internat'l Journal, 2002, pp. 1-9.
Gould et al., "Transformation of Zea mays L. Using Agrobacterium Tumefaciens and to Shoot Apex", Article, Plant Physiol. 1991, 95:426-434.
Horsch et al., "A Simple and General Method for Transferring Genes into Plants", Article, Biological Sciences, vol. 227, Mar. 1985, pp. 1229-1231.
Herman et al., "Retenton of Phytohemagglutinin with Carboxyterminal Tetrapeptide KDEL in the Nuclear Envelope and the Endoplasmic reticulum", Planta, 1990 182:305-312.
Hernalsteens et al., "An Agrobacterium Transformed Cell Culture from the Monocot", Article, The Embro Journal vol. 3 No. 13 pp. 3039-3304, 1984.
Hill et al., "environmental, Ecomomic, and Energetic Costs and Benefits of biodiesel and Ethanol Biofuels", Article, PHAS, No. 30, 103: 11206-11210, Jul. 25, 2006.
Gordon-Kamm et al., "Transformation of Maize Cells and Regeneration of Fertile Transgenic Plants", Article, The Plant Cell, 2:603-618, Amer. Soc. Plant Physiol, Jul. 1990.
International Search Report for International Application No. PCT/US2008/066696.
Karlin, et al., "Applications and Statistics for Multiple High Scoring Segments in Molecular Sequences", Article, Proc. Natl. Acad. Sci., 90:5873-5877, Jun. 1993.
Karlin, et al., "Methods for Assessing the Statistical Significance of Molecular Sequences Features by Using General Scoring Schemes", Article, Proc. Natl. Acad. Sci. 87:2264-2268, Mar. 1990.
Katavic et al., "Protein and Lipid Composition Analysis of Oil Bodies from two Brassica Napus Cultivars", Article, Proteomics, 6:4586-4598, 2006.
Kwak, et al., "A Strong Constitutive Gene Expression System Derived from ibAGP1 Promoter and its Transmit Peptide" Article, Plant Cell Rep 26: 1253-1262, 2007.
Lacey et al., Heterogeneity of the Endoplasmic Reticulum with Respect to Lipid Synthesis in Developing Seeds of Brassica Napus L, Article, Planta 199:545-551 Planta, 1996.
Lotan, et al., "Arabidopsis Leafy Cotyledon 1 is Sufficien tot Induce Embryo Developmen tin Vegetative Cells", Article, Cell 93:1195-1205, Jun. 26, 1998.
Muller, et al., "Stable Transformation of Sunflower (*Helianthus annuus* L.) Using a Non-Meristematic Regeneration protocol and Green Fluorescent Protein as a Vital Marker", Article, Transgenic Research 10:435-444, 2001.

Munro et al., "A C-Terminal Signal prevents Secretion of Luminal ER Proteins", Article, Cell, 48:899-907, Mar. 13, 1987.
Paszkowski et al., Direct Gene Transfer to Plants, Article, the EMBO Journal, No. 3:2717-2722, 1984.
Rasco-Gaunt et al., "Characterisation of the Expression of a Novel Constitutive maize Promoter in Transgenic Wheat and Maize", Article, Plant Cell Rep. 21:569-576, 2003.
Reddy et al., Expression of a Cyanobacterial Desaturase Gene Results in y Linolenic Acid Production in Transgenic Plants, Nat. Biotechnol. 14, 639, 1996.
Samac et al, "A Comparison of Constitutive Promoters for Expression of Transgenes in Alfalfa", Article, Transgenic Research 13:349-361, 2004.
Shrawat et al., "Agrobacterium-Mediated Transformation of Cereals: a Promising Approach Crossing Barriers", Article, Plant Biotechnology Journal, 2006, 4:575-603.
Thelen et al., "Metabolic Engineering of Fatty Acid Biosynthesis in Plants", Article, Metabolic Engineering 4:12-21, 2002.
Tung et al., "Over Expresson of LeNCED1 in Tomato (*Solanum lycopersicum* L.) with the rbcS3C Promoter Allows Recovery of Lines that Accumulate Very High levels of Abscisic Acid and Exhibit Severe Phenotypes", Article, Plant, Cell and environment 2008, 31:968-981.
Sambrook et al., Molecular Cloning, a Laboratory manual, "Southern Hybridization of Radiolabeled Probes to Nucleic Acids Immobilized on Membranes", Book, Third Edition, Protocol 10, CSHL Press, vol. 1, 6.50-6.68.
Usta, "Use of Tobacco Seed Oil Methyl Ester in a Turbocharged Indirect injection Diesel Engine", Article, Elsevier, Biomass and Bioenergy, 28 (2005) 77-86.
Vigeolas et al., "Increasing Seed Oil Content in Oil Seed rap (*Brassica napus* L.) by Over Expression of a Yeasat Glycerol-3-Phosphate Dehydrogenase Under the Control of a Seed Specific Promoter", Article, Plant Biotechnology Journal, 2007, 5:43-441.
Wandelt et al., "Vicilin with Carboxy-Terminal KDEL is Retained in the Endoplasmic Reticulum and Accumulates to High Levels in the Leaves of Transgenic Plants", Article, The Plant Journal, 1992, 2(2):181-192.
Wahlross, et al., "Oleosin Expression and Trafficking During Oil Body Biogenesis in Tobacco Leaf Cells", Article, 2003, Genesis 35:125-132.
Zhao et al. "Agrobacterium-Mediated sorghum Transformation", Article, Plant Molecular biology 44:789, 2000, Kluwer Academic Publishers.
Yamamoto et al., "Genetic Transformation of Duckweed Lemna Gibba and Lemna Minor", Article, Plant 37:349-353, 2001, Society for in Vitro Biology.
Breitler et al., Bt Rice Harbouring Cry Genes Controlled by a Constitutive or Wound Inducible Promoter . . . , Article, Plant Biotech, Jml, 2004, 4:417-430, Blackwell Publishing.

* cited by examiner

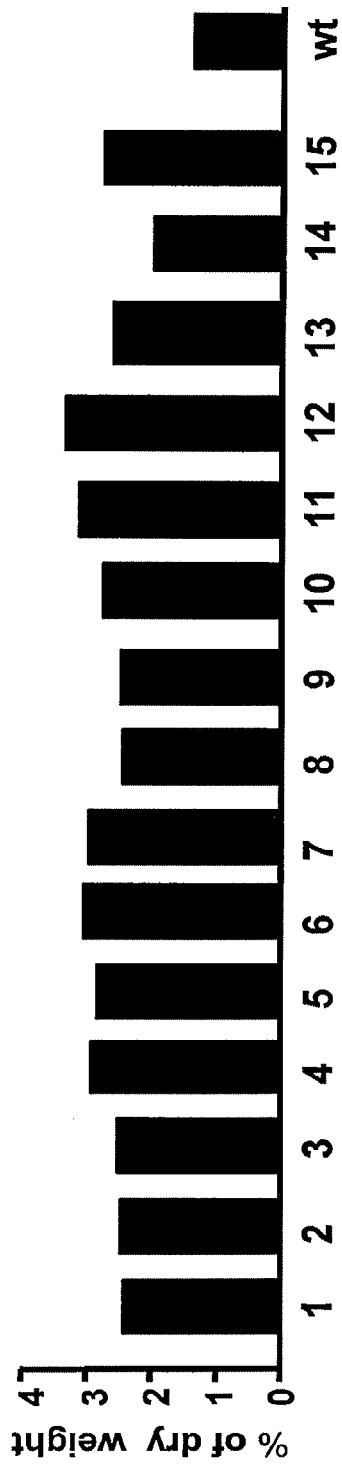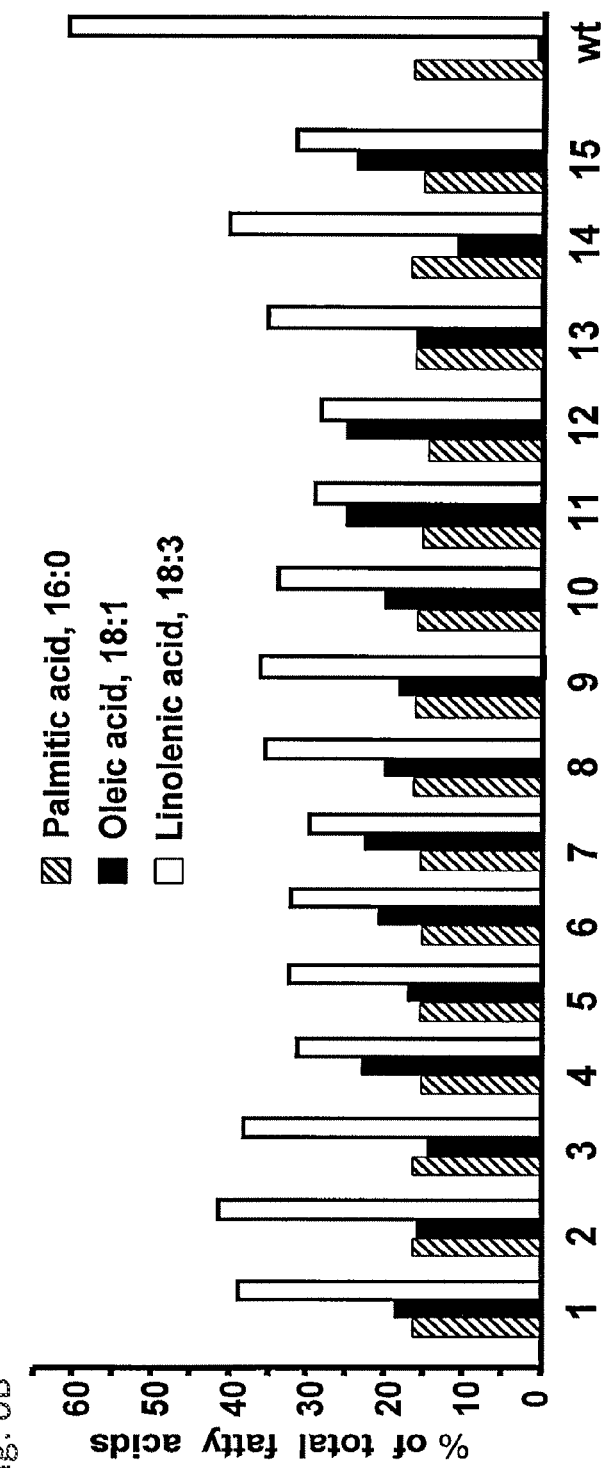

SEQUENCE LISTING

<160> NUMBER OF SEQ ID NOS: 8

<210> SEQ ID NO 1
<211> LENGTH: 1563
<212> TYPE: DNA
<213> ORGANISM: Arabidopsis thaliana

<400> SEQUENCE: 1

```
atggcgattt tggattctgc tggcgttact acggtgacgg agaacggtgg cggagagttc      60
gtcgatcttg ataggcttcg tcgacggaaa tcgagatcgg attcttctaa cggacttctt     120
ctctctggtt ccgataataa ttctccttcg gatgatgttg gagctcccgc cgacgttagg     180
gatcggattg attccgttgt taacgatgac gctcaggaa cagccaattt ggccggagat      240
aataacggtg gtggcgataa taacggtggt ggaagaggcg gcggagaagg aagaggaaac     300
gccgatgcta cgtttacgta tcgaccgtcg gttccagctc atcggagggc gagagagagt     360
ccacttagct ccgacgcaat cttcaaacag agccatgccg gattattcaa cctctgtgta     420
gtagttctta ttgctgtaaa cagtagactc atcatcgaaa atcttatgaa gtatggttgg     480
ttgatcagaa cggatttctg gtttagttca agatcgctgc gagattggcc gcttttcatg     540
tgttgtatat ccctttcgat cttttccttg gctgccttta cggttgagaa attggtactt     600
cagaaataca tatcagaacc tgttgtcatc tttcttcata ttattatcac catgacagag     660
gttttgtatc cagtttacgt caccctaagg tgtgattctg cttttttatc aggtgtcact     720
ttgatgctcc tcacttgcat tgtgtggcta aagttggttt cttatgctca tactagctat     780
gacataagat ccctagccaa tgcagctgat aaggccaatc ctgaagtctc ctactacgtt     840
agcttgaaga gcttggcata tttcatggtc gctcccacat tgtgttatca gccaagttat     900
ccacgttctg catgtatacg gaagggttgg gtggctcgtc aatttgcaaa actggtcata     960
ttcaccggat tcatgggatt tataatagaa caatatataa atcctattgt caggaactca    1020
aagcatcctt tgaaaggcga tcttctatat gctattgaaa gagtgttgaa gctttcagtt    1080
ccaaatttat atgtgtggct ctgcatgttc tactgcttct tccacctttg gttaaacata    1140
ttggcagagc ttctctgctt cggggatcgt gaattctaca aagattggtg gaatgcaaaa    1200
agtgtgggag attactggag aatgtggaat atgcctgttc ataaatggat ggttcgacat    1260
atatacttcc cgtgcttgcg cagcaagata ccaaagacac tcgccattat cattgctttc    1320
ctagtctctg cagtctttca tgagctatgc atcgcagttc cttgtcgtct cttcaagcta    1380
```

```
tgggctttc ttgggattat gtttcaggtg cctttggtct tcatcacaaa ctatctacag    1440
gaaaggtttg gctcaacggt ggggaacatg atcttctggt tcatcttctg cattttcgga   1500
caaccgatgt gtgtgcttct ttattaccac gacctgatga accgaaaagg atcgatgtca   1560
tga                                                                  1563

<210> SEQ ID NO 2
<211> LENGTH: 26
<212> TYPE: DNA
<213> ORGANISM: Artificial
<220> FEATURE:
<223> OTHER INFORMATION: PCR Primer

<400> SEQUENCE: 2
gaaaccatgg cgattttgga ttctgc                                         26

<210> SEQ ID NO 3
<211> LENGTH: 32
<212> TYPE: DNA
<213> ORGANISM: Artificial
<220> FEATURE:
<223> OTHER INFORMATION: PCR Primer

<400> SEQUENCE: 3
atctgcggcc gctgacatcg atcctttcg gt                                   32

<210> SEQ ID NO 4
<211> LENGTH: 1092
<212> TYPE: DNA
<213> ORGANISM: Arabidopsis thaliana

<400> SEQUENCE: 4
atggataact tcttacccct tccctcttct aacgcaaact ctgtccaaga actctctatg    60
gatcctaaca caatcgctc gcacttcaca acagtcccta cttatgatca tcatcaggct    120
cagcctcatc acttcttgcc tccgttttca tacccggtgg agcagatggc ggcggtgatg    180
aatcctcagc cggtttactt atcggagtgt tatcctcaga tcccggttac gcaaaccgga    240
agtgaattcg gttctctggt tggtaatcct tgtttgtggc aagagagagg tggttttctt    300
gatccgcgta tgacgaagat ggcaaggatc aacaggaaaa acgccatgat gagatcaaga    360
aacaactcta gccctaattc tagtccaagt gagttggttg attcaaagag acagctgatg    420
atgcttaact tgaaaaataa cgtgcagatc tccgacaaga aagatagcta ccaacagtcc    480
acatttgata caagaagct tagggttttg tgtgagaagg aattgaagaa cagcgatgtt    540
gggtcactcg ggaggatagt tctaccaaag agagatgcag aagcaaatct tccgaagcta    600
tctgataaag aaggaatcgt tgtacagatg agagatgttt tctctatgca gtcttggtct    660
ttcaaataca gttttggtc caataacaag agcagaatgt atgtcctcga gaacacagga    720
gaatttgtga gcaaaatgg agctgagata ggagacttt taacaatata cgaggacgaa    780
agcaagaatc tctacttcgc catgaatgga aattcgggaa acaaaatga aggaagagaa    840 aatgagtcga gggaaaggaa ccactacgaa gaggcaatgc ttgattacat accaagagac    900
gaagaggaag cttccattgc aatgctcatc ggaaatctaa acgatcacta tcccatccct    960
aacgatctca tggacctcac cactgacctt cagcaccatc aagccacgtc ctcatcaatg    1020
ccacctgagg atcacgcgta cgtgggttca tccgatgatc aggtgagctt taacgacttt    1080
gagtggtggt ga                                                        1092
```

-continued

<210> SEQ ID NO 5
<211> LENGTH: 34
<212> TYPE: DNA
<213> ORGANISM: Artificial
<220> FEATURE:
<223> OTHER INFORMATION: PCR Primer

<400> SEQUENCE: 5
tagatctgcc atggataact tcttaccctt tccc                                   34

<210> SEQ ID NO 6
<211> LENGTH: 38
<212> TYPE: DNA
<213> ORGANISM: Artificial
<220> FEATURE:
<223> OTHER INFORMATION: PCR Primer

<400> SEQUENCE: 6
tagatcttca ccaccactca aagtcgttaa agctcacc                               38

<210> SEQ ID NO 7
<211> LENGTH: 520
<212> TYPE: PRT
<213> ORGANISM: Arabidopsis thaliana

<400> SEQUENCE: 7

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                    325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Asn Ala Lys
385                 390                 395                 400

Ser Val Gly Asp Tyr Trp Arg Met Trp Asn Met Pro Val His Lys Trp
                    405                 410                 415

Met Val Arg His Ile Tyr Phe Pro Cys Leu Arg Ser Lys Ile Pro Lys
            420                 425                 430

Thr Leu Ala Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                    485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520

<210> SEQ ID NO 8
<211> LENGTH: 363
<212> TYPE: PRT
<213> ORGANISM: Arabidopsis thaliana

<400> SEQUENCE: 8

Met Asp Asn Phe Leu Pro Phe Pro Ser Ser Asn Ala Asn Ser Val Gln
1               5                   10                  15

Glu Leu Ser Met Asp Pro Asn Asn Asn Arg Ser His Phe Thr Thr Val
            20                  25                  30

Pro Thr Tyr Asp His His Gln Ala Gln Pro His His Phe Leu Pro Pro
        35                  40                  45

Phe Ser Tyr Pro Val Glu Gln Met Ala Ala Val Met Asn Pro Gln Pro
    50                  55                  60

Val Tyr Leu Ser Glu Cys Tyr Pro Gln Ile Pro Val Thr Gln Thr Gly
65                  70                  75                  80

Ser Glu Phe Gly Ser Leu Val Gly Asn Pro Cys Leu Trp Gln Glu Arg
                85                  90                  95

Gly Gly Phe Leu Asp Pro Arg Met Thr Lys Met Ala Arg Ile Asn Arg
            100                 105                 110

-continued

```
Lys Asn Ala Met Met Arg Ser Arg Asn Asn Ser Ser Pro Asn Ser Ser
            115                 120             125

Pro Ser Glu Leu Val Asp Ser Lys Arg Gln Leu Met Met Leu Asn Leu
    130                 135             140

Lys Asn Asn Val Gln Ile Ser Asp Lys Lys Asp Ser Tyr Gln Gln Ser
145             150                 155                 160

Thr Phe Asp Asn Lys Lys Leu Arg Val Leu Cys Glu Lys Glu Leu Lys
            165                 170             175

Asn Ser Asp Val Gly Ser Leu Gly Arg Ile Val Leu Pro Lys Arg Asp
            180                 185             190

Ala Glu Ala Asn Leu Pro Lys Leu Ser Asp Lys Glu Gly Ile Val Val
            195                 200             205

Gln Met Arg Asp Val Phe Ser Met Gln Ser Trp Ser Phe Lys Tyr Lys
            210                 215             220

Phe Trp Ser Asn Asn Lys Ser Arg Met Tyr Val Leu Glu Asn Thr Gly
225                 230                 235             240

Glu Phe Val Lys Gln Asn Gly Ala Glu Ile Gly Asp Phe Leu Thr Ile
            245                 250             255

Tyr Glu Asp Glu Ser Lys Asn Leu Tyr Phe Ala Met Asn Gly Asn Ser
            260                 265             270

Gly Lys Gln Asn Glu Gly Arg Glu Asn Glu Ser Arg Glu Arg Asn His
        275                 280             285

Tyr Glu Glu Ala Met Leu Asp Tyr Ile Pro Arg Asp Glu Glu Glu Ala
        290                 295             300

Ser Ile Ala Met Leu Ile Gly Asn Leu Asn Asp His Tyr Pro Ile Pro
305             310                 315                 320

Asn Asp Leu Met Asp Leu Thr Thr Asp Leu Gln His His Gln Ala Thr
                325                 330             335

Ser Ser Ser Met Pro Pro Glu Asp His Ala Tyr Val Gly Ser Ser Asp
            340                 345             350

Asp Gln Val Ser Phe Asn Asp Phe Glu Trp Trp
            355                 360
```

ENGINEERED BIOMASS WITH INCREASED OIL PRODUCTION

FIELD OF THE INVENTION

This invention relates to genetically modified plants having an increased amount of oil as compared to their non-genetically modified counterparts. The genetically modified plant can have increased oil production, increased oil accumulation, or both. Oils extracted from such plants may be used for industrial purposes such as heating, producing bio-fuels such as biodiesel fuel, or lubricating applications.

BACKGROUND

Growing demand for alternative sources of energy can be fulfilled at least in part with a renewable supply of plant-derived biofuel oil and/or ethanol. To be a viable alternative to fossil fuels, the biofuel should provide a net energy gain in production, have environmental benefits, be economically competitive, and producible in large quantities without reducing food supplies, a current unintended byproduct of existing biofuel production.

The two predominant U.S. alternative transportation fuels, relative to fossil gasoline and diesel, are ethanol fermented from corn grain starch and biodiesel oil extracted from soybean seeds. Both corn and soybean are staple crops, on which national food supply significantly relies. Corn ethanol yields 25% more energy than the energy invested in its production, whereas biodiesel yields 93% more. Relative to the fossil fuels they displace, greenhouse gas emissions are reduced 12% by the production and combustion of ethanol and 41% by biodiesel. Biodiesel also releases fewer air pollutants per net energy gain than ethanol. These advantages of biodiesel over ethanol come from lower agricultural inputs and more efficient conversion of feedstocks to fuel. However, according to a recent estimation by Hill et al. (Environmental, economic, and energetic costs and benefits of biodiesel and ethanol biofuels. Proc Natl Acad Sci USA. 2006, 103(30):11206-11210), even dedicating all U.S. corn and soybean production to biofuels would meet only 12% of the gasoline demand and 6% of the demand for diesel.

Ideally, what is needed to support national alternative transportation fuel demands is biofuels produced from low-input biomass grown on agriculturally marginal land, using high-biomass plant species that are not involved in the food supply chain.

Growing demand for alternative sources of energy can be fulfilled with a renewable supply of plant-derived fuel oil and/or ethanol. Plants represent a significant source of biofuel vegetable oil because many species accumulate oil lipids as major storage components in seeds. The main form of vegetative storage oil in seeds, which represent, depending on the species, 15-50% of seed weight, is triacylglycerol (TAG). However, the primary substrate for oil synthesis are the carbohydrates generated in green photosynthetic tissues (leaves and stems) that are subsequently metabolized in chloroplasts to produce free fatty acids and acetyl-CoA units, the basic building blocks for TAG. Therefore, plant leaves are the main place of building block synthesis for TAG, and as it has been experimentally examined, the amount of TAG accumulated in oil seeds may be in part determined by the amount of fatty acid produced in plastids. (Bao X, Ohlrogge J. Supply of fatty acid is one limiting factor in the accumulation of triacylglycerol in developing embryos. Plant Physiol. 1999, 120:1057-62). Final storage of TAG occurs in seeds in small spherical organelles termed oil bodies (Heterogeneity of the endoplasmic reticulum with respect to lipid synthesis in developing seeds of *Brassica napus* L. Planta, 1996, 208:503-511; Wahlroos T, Soukka J, Denesyuk A, Wahlroos R, Korpela T, Kilby N J. Oleosin expression and trafficking during oil body biogenesis in tobacco leaf cells. Genesis. 2003, 35(2):125-132; Katavic V, Agrawal G K, Hajduch M, Harris S L, Thelen J J. Protein and lipid composition analysis of oil bodies from two *Brassica napus* cultivars. Proteomics. 2006, 16: 4586-4598). Only about 0.2-0.3% of leaf biomass is represented by TAG.

With the advances in molecular biology and plant transformation technology, the metabolic engineering of fatty acids and vegetable oils has become possible (Gunstone F D, Pollard M. Vegetable oils with fatty acid changes by plant breeding or genetic modification. In F D Gunstone, ed, Structured and Modified Lipids. Marcel Dekker, New-York, pp 155-184 (2001); Thelen J J, Ohlrogge J B. Metabolic engineering of fatty acid biosynthesis in plants. Metabolic Engineering 4, 12-21 (2002)). Plant oils represent some of the first successes in the design of improved plant products, and tobacco has been used as one of the first model plants to express genetically engineered fatty acids (Cahoon E B, Shanklin J, Ohlrogge J B. Expression of a coriander desaturase results in petroselinic acid production in transgenic tobacco. Proc Natl Acad Sci USA. 1992 89(23):11184-8; Reddy A S, Thomas T L. Expression of a cyanobacterial delta 6-desaturase gene results in gamma-linolenic acid production in transgenic plants. Nat Biotechnol. 1996, 14:639-642). The plant tissues that usually do not accumulate high amounts of oil still contain the enzymes used to synthesize these storage compounds.

High biomass plants, particularly broad leaf high biomass plants, have great biofuel potential. Plants that can yield between 100-400 tons/acre of low-cost, high-value biomass materials are particularly useful especially when there are none of the high costs, labor requirements, chemical inputs, or geographic restrictions associated with low biomass plant production.

While almost all plants have been investigated as alternative energy resources, tobacco (*Nicotiana tabacum* and other species from the *Nicotiana* genus) has been mostly overlooked. Similar to hardwood trees, tobacco will coppice or re-sprout from its stump after it has been cut. Coppicing makes multiple harvests in a year possible, enabling it to produce very high biomass tonnage. Tobacco thrives on different kinds of soil in a wide range of environments. The yield of tobacco seeds amounts to 600 kg/ha. The oil content in tobacco seed ranges between 36% and 41% by weight (Giannelos P N, Zannikos S, Stournas S, Lois E, Anastoloulos G. Tobacco seed oil as an alternative diesel fuel: physical and chemical properties. Industrial Crops and Products 2002, 16:1-9), indicating the existence of potent oil synthesis machinery, comparable to one of the traditional oil producers, such as soybean or rapeseed. Recent experiments indicated that tobacco seed oil can partially substitute petroleum diesel fuel at most operating conditions in terms of performance parameters and emissions without any engine modification and preheating of the blends (Gunstone F. D., Pollard M., Vegetable oils with fatty acid changes by plant breeding or genetic modification. In F. D. Gunstone, ed, Structured and Modified Lipids. Marcel Dekker, New-York, pp 155-184 (2001); Usta N. Use of tobacco seed oil methyl ester in a turbocharged indirect injection diesel engine. Biomass and Bioenergy 2005, 28: 77-86).

While the oil is accumulated at such high levels in seeds, (tobacco seed oil is used for some cosmetic and pharmaceutical needs), oil deposition in leaves is much lower, making the downstream oil extraction rather expensive. However, extraction of oil from leaf biomass might be cost-efficient in the case of significant improvement of oil content in leaves. This invention provides a technology for increasing oil yield from the green biomass of plants using an innovative biotechnology approach.

SUMMARY OF THE INVENTION

This invention is a genetically modified plant having green biomass, wherein said genetically modified plant has been genetically modified such that its green biomass has at least 10-fold the amount by weight of triacylglycerols, and at least two-fold and preferably three-fold the amount by weight of total extractable fatty acids as compared to the green biomass in its non-genetically modified counterpart.

In another aspect of this invention the plant produces an oil that has a fatty acid composition different from that of its non-genetically modified counterpart, which oil contains at least 20% by weight of oleic acid, preferably at least 30% by weight of oleic acid.

In one embodiment, the genetically modified plant is selected from the group consisting of tobacco, maize, pea, canola, Indian mustard. millet, sorgum, sunflower, hemp, switchgrass, duckweed, sugarcane, sorghum, and sugar beet.

In one aspect, the present invention relates to a genetically modified plant that has been genetically modified to provide increased expression of one or more genes encoding one or more enzymes for oil biosythesis which can increase the amount of oil in the green biomass of the genetically modified plant as compared to the green biomass of its non-genetically modified counterpart. In one embodiment, the genetically modified plant has increased expression of a gene encoding a polypeptide selected from the group consisting of a hydrolase and an acyl transferase and wherein the gene is operably linked to a promoter. In another embodiment, the polypeptide is an esterase, a thioesterase, lauryl-acyl carrier protein thioesterase, acyl CoA:diacylglycerol acyltransferase or Sn-2 acyltransferase. In another embodiment, the gene encodes a polypeptide comprising SEQ ID NO: 7. In another embodiment, the promoter is selected from the group consisting of constitutive promoters, regulatable promoters, and inducible promoters. In another embodiment, the promoter is selected from the group consisting of CaMV 35S, Rubisco, a histone gene promoter, ubiquitin, criptic tCUP, VR-ACS1, CsVMV, ScBV, eLF4A-10, and ibAGP1

In another embodiment, the genetically modified plant has increased expression of a gene, wherein the gene encodes a transcription factor, and wherein the transcription factor regulates seed development in the plant and the transcription factor is operably linked to an inducible promoter. In another embodiment, the transcription factor is encoded by one or more selected from LEC1, LEC2, FUS3 and WR1. In another embodiment, the gene encodes a polypeptide comprising SEQ ID NO: 8. In another embodiment, the gene comprises a polynucleotide sequence comprising SEQ ID NO: 4. In another embodiment, the inducible promoter is selected from a chemically-inducible promoter and a physiologically-inducible promoter. Preferred chemically-inducible promoters can be selected from a tetracycline-inducible promoter, an ethanol-inducible promoter, and a hormone-inducible promoter Preferred physiologically-inducible promoters can be selected from a heat-inducible promoter, a wound-inducible promoter, a senescence-inducing promoter, and a maturation-inducing promoter.

In one aspect the present invention relates to a genetically modified plant having an increased amount of oil as compared to a non-genetically modified plant, and wherein the genetically modified plant is genetically modified to stimulate increased oil accumulation in green plant tissues as compared to a non-genetically modified plant wherein the genetically modified plant has increased expression of (a) at least one first gene, wherein the first gene encodes a polypeptide selected from the group consisting of a hydrolase and an acyl transferase and wherein the first gene is operably linked to a first promoter selected from the group consisting of a constitutive promoter, regulatable promoter, or an inducible promoter; and (b) at least one second gene, wherein the second gene encodes a transcription factor, wherein the transcription factor regulates seed development of the genetically modified plant, and wherein the second gene is operably linked to a second promoter wherein the second promoter is an inducible promoter.

Yet another aspect of this invention is the production of a biodiesel fuel that involves the extraction of the oil from a plant of this invention and the transesterification of that oil to produce biodiesel fuel.

BRIEF DESCRIPTION OF THE DRAWINGS

FIG. 6(A) represents the results of quantitative gas chromatography (GC) analysis of total fatty acids (% of dry weight) in plants (1-15) of this invention compared to their genetically unmodified counterpart (wt).

FIG. 6(B) represents the results of GC analysis of relative amounts of particular fatty acids in plants (1-15) of this invention compared to their genetically unmodified counterpart (wt).

DETAILED DESCRIPTION OF THE INVENTION

Figure 1:
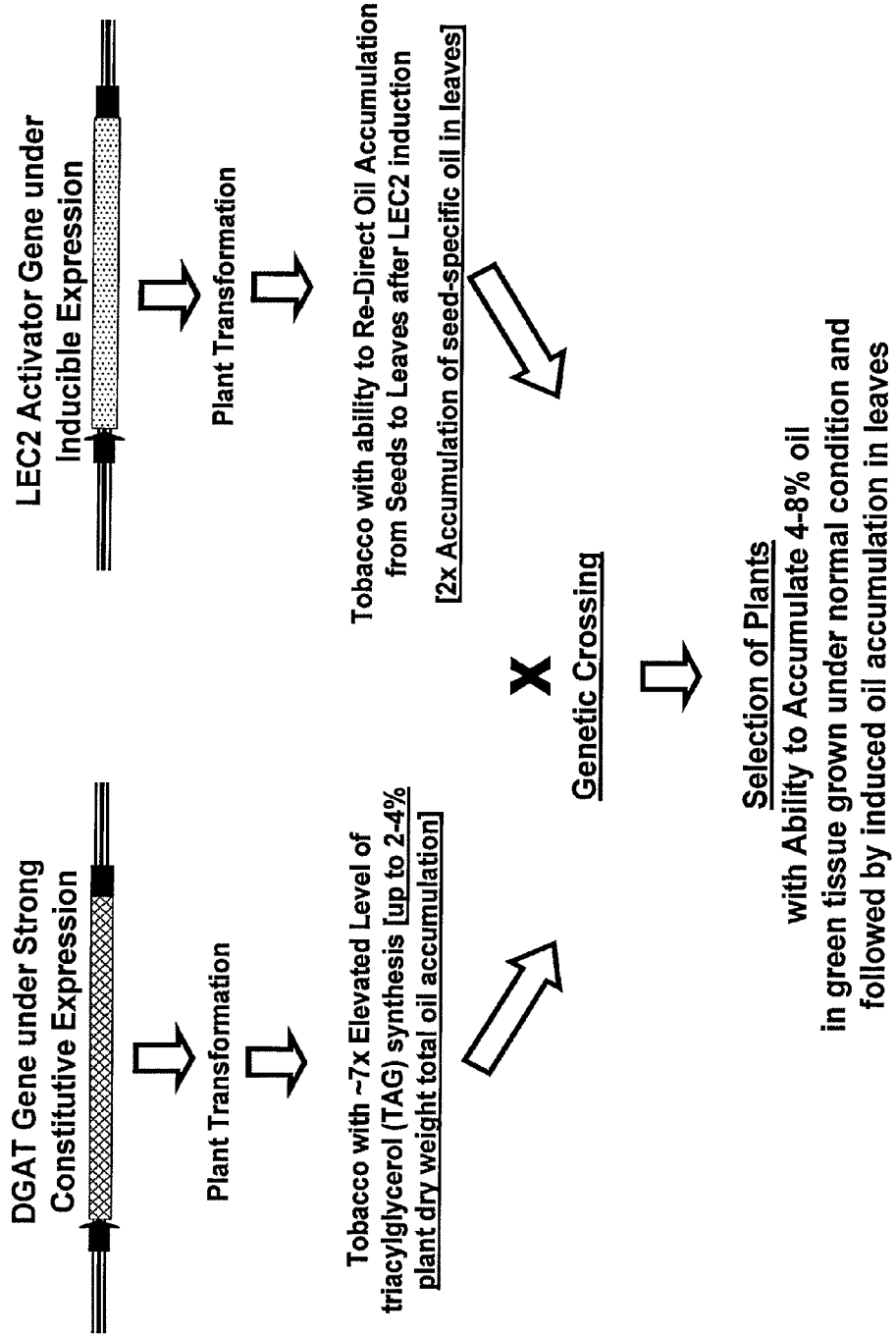
FIG. 1 is a flow chart for a first strategy to achieve oil level increase in plants.

This invention provides a genetically modified plant having an increased amount of oil in its green biomass as compared to the green biomass of its non-genetically modified counterpart.

As used herein, the term "plant" refers to whole plants, plant organs (i.e., leaves, stems, flowers, roots, etc.), seeds and plant cells (including tissue culture cells), and progeny of same. The class of plants that can be used in the method of the invention is generally as broad as the class of higher plants amenable to transformation techniques, including both monocotyledonous and dicotyledonous plants, as well as certain lower plants such as algae. Suitable plants include plants of a variety of ploidy levels, including polyploid, diploid and haploid. The term "transgenic plant" refers to a plant modified to express one or more genes. Although a variety of plants may be used in this invention, the genetically modified plants of the present invention are preferably selected from the group of tobacco, maize, pea, canola, Indian mustard, millet, sunflower, hemp, switchgrass, duckweed, sugarcane, sorghum, and sugar beet. Preferably the plant used in this invention is selected from tobacco, hemp, switchgrass and duckweed because they are not food-generating crops for humans and because they can be grown on agriculturally marginal land.

The term "green biomass" means those parts of plants involved in photosynthesis (e.g., and stems and leaves of higher plants and aquatic plants such as algae).

The term "genetically modified" refers to plants in which a gene has been added or modified so as to provide the desired characteristics above.

In one embodiment, the genetically modified plant has been modified to increase the amount of oil in the entire plant compared to a non-genetically modified plant. The term "entire plant" refers to a higher total amount of oil in the plant as a whole. This can result from higher amounts of oil in some or all of the plant tissues.

The term "increased amount of oil" refers to plant oils suitable for use as biofuels. In particular, vegetable oils that may be present as triacylgycerol (TAG) and other oils indigenous to plants, particularly high biomass plants. A number of criteria may be used to determine if a given vegetable oil is suitable for use in the present invention, including flash point, energy content, viscosity, combustion products, and estimated costs for growing the host plant and extracting the oil.

In another embodiment, the genetically modified plant has roots wherein there is increased oil storage in the roots as compared to the non-genetically modified plant. In another embodiment, the genetically modified plant has stems wherein there is increased oil storage in the stems as compared to the non-genetically modified plant.

In one embodiment, the oil is a vegetable oil. In another embodiment, the oil is a triacylglycerol. In another embodiment, the oil is similar or identical to a seed oil of the non-genetically modified counterpart.

In one aspect, the present invention relates to a genetically modified plant that has been genetically modified to provide increased expression of a gene encoding a polypeptide which can increase the amount of oil in the green biomass of the genetically modified plant as compared to the green biomass of its non-genetically modified counterpart.

As used herein, the term "gene" refers to an element or combination of elements that are capable of being expressed in a cell, either alone or in combination with other elements. In general, a gene comprises (from the 5' to the 3' end): (1) a promoter region, which includes a 5' non-translated leader sequence capable of functioning in plant cells; (2) a structural gene or polynucleotide sequence, which codes for the desired protein; and (3) a 3' non-translated region, which typically causes the termination of transcription and the polyadenylation of the 3' region of the RNA sequence. Each of these elements is operably linked by sequential attachment to the adjacent element. A gene comprising the above elements is inserted by standard recombinant DNA methods into a plant expression vector.

As used herein, "polypeptide" is used interchangeably with protein, peptide and peptide fragments. "Polypeptides" include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. The polypeptides include natural peptides, recombinant peptides, synthetic peptides, or a combination thereof.

In one embodiment, the genetically modified plant has increased expression of a gene encoding a polypeptide wherein the polypeptide is an enzyme involved in lipid metabolism, in particular, enzymes involved in increased oil accumulation (Beisson et al., *Plant Physiol.*, 132(2), 681-697 (2003); Thelen and Ohlrogge, *Metabolic Engineering*, 4, 12-21 (2002); Baud et al, *Plant J.*, 33(1), 75-86 (2003); Vigeolas et al., *Plant Biotechnol. J.*, 5(3), 431-41 (2007)). In preferred embodiments, the enzyme is selected from the group consisting of a hydrolase and an acyl transferase and wherein the gene is operably linked to a promoter.

As used herein "promoter" refers to a region of a DNA sequence active in the initiation and regulation of the expression of a structural gene. This sequence of DNA, usually upstream to the coding sequence of a structural gene, controls the expression of the coding region by providing the recognition for RNA polymerase and/or other elements required for transcription to start at the correct site.

In another embodiment, the polypeptide is an esterase, a thioesterase, lauryl-acyl carrier protein thioesterase, acyl CoA:diacylglycerol acyltransferase or Sn-2 acyltransferase. Preferably, a diacylglycerol acyltransferase of plant, yeast or animal origin is used. In another embodiment, the gene encodes a polypeptide comprising SEQ ID NO: 7. In another embodiment, the gene comprises a polynucleotide sequence comprising SEQ ID NO: 1 (*Arabidopsis thaliana* diacylglycerol acyltransferase) or substantially homologous sequences.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not substantially alter the expressed polypeptide's activity.

As disclosed herein, "substantially homologous sequences" include those sequences which have at least about 50%, homology, preferably at least about 60%, more preferably at least about 70% homology, even more preferably at least about 80% homology, and most preferably at least about 95% or more homology to the polynucleotides of the invention.

In another embodiment, the promoter is selected from the group consisting of constitutive promoters, regulatable promoters, and inducible promoters. Suitable promoters include CaMV 35S and Rubisco.

In another embodiment, the promoter is selected from the group of promoters that direct constitutive gene expression throughout green plant tissues, particularly leaves and stems. This group is exemplified by the strong promoters of plant virus origin, such as the 35S promoter from cauliflower mosaic virus (CaMV), the cassava vein mosaic virus (CsVMV) promoter, the sugarcane bacilliform badnavirus (ScBV) promoter, or similar plant virus promoters (Samac D A, Tesfaye M, Dornbusch M, Saruul P, Temple S J. A comparison of constitutive promoters for expression of transgenes in alfalfa (*Medicago sativa*). Transgenic Res. 2004 August; 13(4):349-61.) In addition such promoter can be a promoter of small subunit of ribulose-1,5-bisphosphate carboxylase/oxygenase (Rubisco), that drives transgene in a light-responsive and circadian manner (Tung S A, Smeeton R, White C A, Black C R, Taylor I B, Hilton H W, Thompson A J. Over-expression of LeNCED1 in tomato (*Solanum lycopersicum* L.) with the rbcS3C promoter allows recovery of lines that accumulate very high levels of abscisic acid and exhibit severe phenotypes. Plant Cell Environ. 2008 Apr. 23). Such promoter can also be selected from a histone gene promoter, such as H2B promoter (Rasco-Gaunt S, Liu D, Li C P, Doherty A, Hagemann K, Riley A, Thompson T, Brunkan C, Mitchell M, Lowe K, Krebbers E, Lazzeri P, Jayne S, Rice D. Characterization of the expression of a novel constitutive maize promoter in transgenic wheat and maize. Plant Cell Rep. 2003 February; 21(6):569-760; In addition such promoter can be selected from tobacco eLF4A-10 promoter (Tian L, Wu K, Hannam C, Latoszek-Green M, Sibbald S, Hu M, Brown D C, Miki B. Analysis and use of the tobacco eIF4A-10 promoter elements for transgene expression. J Plant Physiol. 2005 December; 162(12):1355-66) or a tobacco cryptic constitutive promoter, tCUP (Foster E, Hattori J, Labbé H, Ouellet T, Fobert P R, James L E, Iyer V N, Miki B L. A tobacco cryptic constitutive promoter, tCUP, revealed by T-DNA tagging. Plant Mol Biol. 1999 September; 41(1):45-55.). Another such promoter is the ibAGP1 promoter (Kwak M S, Oh M J, Lee S W, Shin J S, Paek K H, Bae J M. A strong constitutive gene expression system derived from ibAGP1 promoter and its transit peptide. Plant Cell Rep. 2007 August; 26(8):1253-62) or a promoter that controls the expression of VR-ACS1 from mung bean (Cazzonelli C I, McCallum E J, Lee R, Botella J R. Characterization of a strong, constitutive mung bean (*Vigna radiata* L.) promoter with a complex mode of regulation in planta. Transgenic Res. 2005 December; 14(6):941-67). Another such promoter is a ubiquitin promoter (Belknap W, Rockhold D, McCue K. pBINPLUS/ARS: an improved plant transformation vector based on pBINPLUS. Biotechniques. 2008 May; 44(6):753-6.)

In another embodiment, the genetically modified plant has increased expression of a gene encoding a transcription factor which regulates seed development in the plant. These transcription factors may be involved in a variety of activities in the plant. In particular, such transcription factors may be necessary to turn on the embryogenesis program which leads to seed development and maturation. Preferably, the transcription factor is operably linked to an inducible promoter. In another embodiment, the transcription factor is LEC2 (Lotan T, Ohto M, Yee K M, West M A, Lo R, Kwong R W, Yamagishi K, Fischer R L, Goldberg R B, Harada J J. *Arabidopsis* LEAFY COTYLEDON1 is sufficient to induce embryo development in vegetative cells. Cell. 1998 93(7): 1195-205) or LEC1, FUS3 or WR1. In another embodiment, the gene encodes a polypeptide comprising SEQ ID NO: 8. In another embodiment, the gene comprises a polynucleotide sequence comprising SEQ ID NO: 4. In another embodiment, the promoter is selected from the group consisting of a wound-inducible promoter, a tetracycline-inducible promoter, and an ethanol-inducible promoter.

In one aspect, the present invention relates to a genetically modified plant having an increased amount of oil as compared to its non-genetically modified counterpart, and wherein the genetically modified plant is genetically modified to stimulate increased oil accumulation in green plant tissues as compared to its non-genetically modified counterpart. This genetically modified plant preferably has increased expression of a first gene, which increases oil production in the plant, such as a polypeptide selected from the group consisting of a hydrolase and an acyl transferase. This first gene is operably linked to a first promoter which regulates expression of the gene, such as a promoter selected from the group consisting of a constitutive promoter, regulatable promoter, or an inducible promoter. This genetically modified plant will also include a second gene, which encodes a transcription factor which regulates seed development of the genetically modified plant. The second gene is operably linked to a second promoter, preferably an inducible promoter.

Figure 2:
FIG. 2 is a flow chart for a second strategy to achieve oil level increase in plants.
Figure 2:
Figure 2:
Figure 2:
Figure 2:
Figures 3A, 3B:
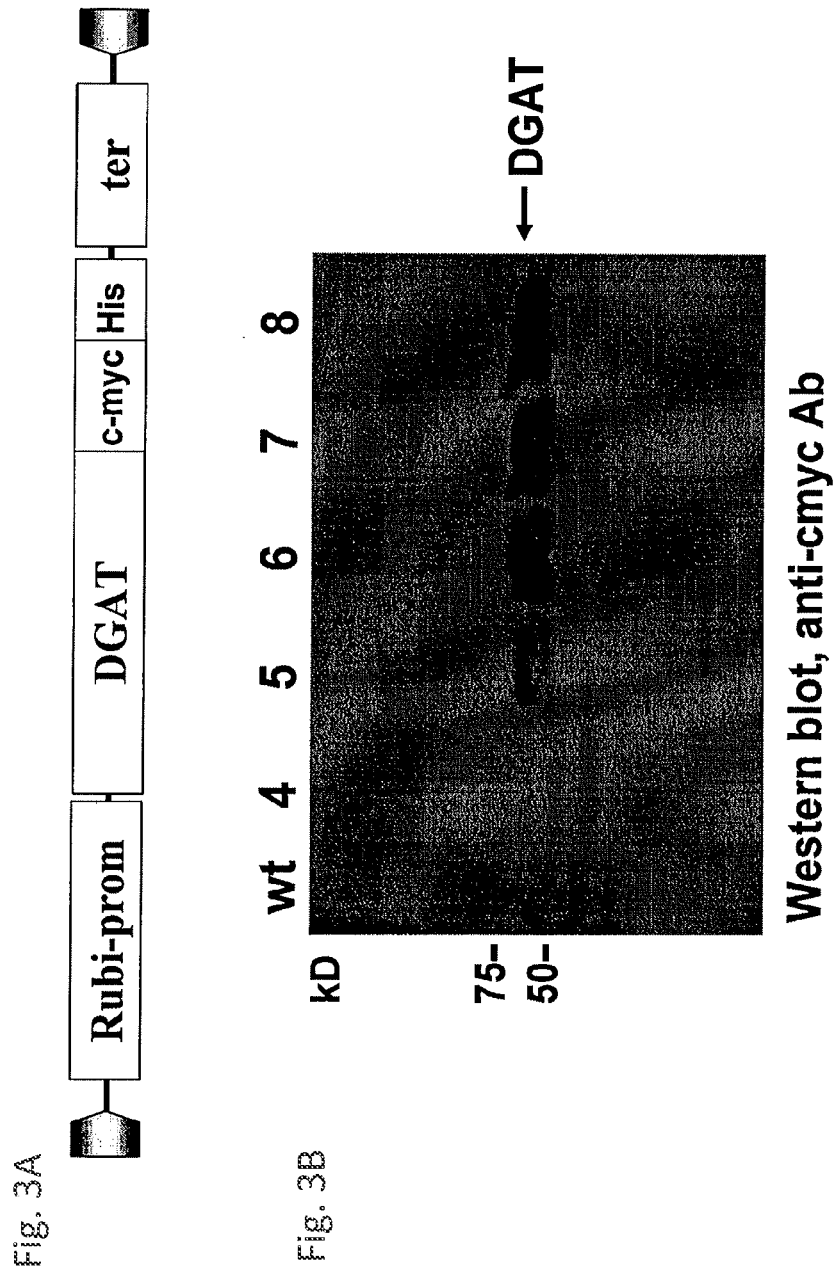
FIG. 3A is a schematic representation of DGAT expression cassette. Rubi-prom, Rubisco promoter; DGAT—polynucleodite sequence coding for DGAT enzyme; c-myc and His—tags for protein detection; ter—nos-terminator.
FIG. 3B is a western blot of protein isolated from selected tobacco plants (nos. 4-8) showing expression of DGAT protein as detected by anti-cmyc tag antibodies as compared to unmodified tobacco, *Nicotiana tabacum* ("wt").

The first and second genes can be introduced in any order into the plant. For example, the first gene can be introduced into plant cells followed by selection of cells expressing high levels of the first gene. Optionally, these plant cells can be used to regenerate the plant at this stage. These plant cells can then be transfected with the second gene, followed by selection of cells expressing high levels of the second gene. Such a strategy can also be employed transfecting the second first, and the first gene last. See FIG. 2.

Another strategy employs a single transfection of both the first and second genes into the plant. The first and second genes can be transduced in a single vector or in two separate vectors.

Cells are then selected that express both genes at high levels, followed by regeneration of the plant cells into plants.

Another strategy employs separate transfections of the two genes into two different sets of plant cells, followed by regeneration of both sets of plant cells into plants. These transgenic plants are then genetically crossed with each other in order to generate a transgenic plant comprising both genes. See FIG. 1.

According to another aspect, the invention provides plant expression vectors carrying the gene constructs of the invention. The gene constructs of the invention comprise polynucleotides encoding hydrolase enzymes, acyl transferase enzymes, and transcription factors, for example lauryl-acyl carrier protein thioesterase, acyl CoA:diacylglycerol acyltransferase, Sn-2 acyltransferase, and LEC2. The regulatory control elements are operably linked to polynucleotides encoding hydrolase enzymes, acyl transferase enzymes, and transcription factors genes. The function of the regulatory control elements, by way of example and not limitation, includes avoiding homology-based gene silencing, increasing hydrolase enzymes, acyl transferase enzymes, and transcription factors gene expression levels, and inducing compartment-specific accumulation, among others.

In one embodiment, the regulatory control elements are operably linked to polynucleotides encoding hydrolase enzymes, acyl transferase enzymes, and transcription factors or both. In another embodiment, the regulatory control elements are operably linked to polynucleotides encoding hydrolase enzymes, acyl transferase enzymes, and transcription factors. In one embodiment, the regulatory control elements comprise a translation alfalfa mosaic virus untranslated leader sequence AMV activator, an ER retention signal KDEL, or both.

Expression vectors are defined herein as DNA sequences that are required for the transcription of cloned copies of genes and the translation of their mRNAs in an appropriate host. Such expression vectors are used to express eukaryotic and prokaryotic genes in plants. Expression vectors include, but are not limited to, cloning vectors, modified cloning vectors, specifically, designed plasmids or viruses.

According to one embodiment of the invention, there are provided plant expression vectors containing one or more gene constructs of the invention. The plant expression vectors of the invention contain the necessary elements to accomplish genetic transformation of plants so that the gene constructs are introduced into the plant's genetic material in a stable manner, i.e., a manner that will allow the genes to be passed on to the plant's progeny. The design and construction of the expression vector influence the integration of the gene constructs into the plant genome and the ability of the genes to be expressed by plant cells.

Preferred among expression vectors are vectors carrying functionally complete hydrolase enzymes, acyl transferase enzymes, and transcription factors, for example lauryl-acyl carrier protein thioesterase, acyl CoA:diacylglycerol acyltransferase, Sn-2 acyltransferase, and LEC2.

Many vector systems are available for the expression of hydrolase enzymes, acyl transferase enzymes, and transcription factors genes in host cells. In one embodiment, hydrolase enzymes and transcription factors are co-expressed in the same cells. In one embodiment, acyl transferase enzymes and transcription factors are co-expressed in the same cells. The co-expression can occur by using either the same or different plasmids in the same host.

Polynucleotides encoding hydrolase enzymes and transcription factors are placed under the control of promoters. The hydrolase enzyme is placed under the control of either an inducible or constitutive promoter. The transcription factor is placed under the control of an inducible promoter. The expression vectors are then transformed into either the same cells, or different cells. Using selectable markers the cells that express the genes are selected.

Polynucleotides encoding acyl transferase enzymes and transcription factors are placed under the control of promoters. The acyl transferase enzyme is placed under the control of either an inducible or constitutive promoter. The transcription factor is placed under the control of an inducible promoter. The expression vectors are then transformed into either the same cells, or different cells. Using selectable markers the cells that express the genes are selected.

In one embodiment, at least one expression vector carrying (a) at least one gene having polynucleotides encoding ahydrolase enzyme and an acyl transferase enzyme, and at least one second gene encoding a transcription factor is used. The first gene is operably linked to a first promoter that is either a constitutive promoter, a regulatable promoter or an inducible promoter. And the second gene is operably linked to a second promoter that is selected from an inducible promoter.

This invention also is a method of making biofuels from plants transformed according to the teachings of this invention. To make biofuels involve extraction of oils from such plants and converting oils to biofuels. Independent of the type of plant, there are several methods for extracting oils from green biomass. One way is physical extraction, which often does not use solvent extraction. It is a "traditional" way using several different types of mechanical extraction. Expeller pressed extraction is a common type, as are the screw press and ram press extraction methods. The amount of oil extracted using these methods varies widely, depending upon the plant material and the mechanical process employed. Mechanical extraction is typically less efficient than solvent extraction described below.

In solvent extraction, an organic solvent (e.g., hexane) is mixed with at least the genetically modified plant green biomass, preferably after the green biomass is dried and ground. Of course, other parts of the plant besides the green biomass (e.g., oil-containing seeds) can be ground and mixed in as well. The solvent dissolves the oil in the biomass and the like, which solution is then separated from the biomass by mechanical action (e.g., with the pressing processes above). This separation step can also be performed by filtration (e.g., with a filter press or similar device) or centrifugation etc. The organic solvent can then be separated from the oil (e.g., by distillation). This second separation step yields oil from the plant and can yield a re-usable solvent if one employs conventional vapor recovery.

Biodiesel oil can be made from oils extracted from plants transformed according to this invention. Biodiesel oil is currently produced from soybean seeds following strict federal specifications (ASTM D6751). Conventionally, biodiesel is made through transesterification process whereby vegetable oil is reacted with methanol in the presence of sodium hydroxide. The process results in producing two products—methyl esters (the chemical name for biodiesel) and glycerin (a valuable byproduct usually sold to be used in soaps and other products). This conventional process can be adapted to the production of biofuel oil from tobacco green biomass (or other green biomass from other plants transformed in accordance with this invention). Caustic compounds and water are added to the oil before carrying out the transesterification step in a well-established industry process known as "alkali refining" (Ericson, 1995).

As to plants transformed according to this invention, specifically designed expression vectors can allow the shuttling of DNA between hosts, such as between bacteria and plant cells. According to one embodiment of the invention, the expression vector contains an origin of replication for autonomous replication in host cells, selectable markers, a limited number of useful restriction enzyme sites, active promoter(s), and additional regulatory control sequences.

Preferred among expression vectors, in certain embodiments, are those expression vectors that contain cis-acting control regions effective for expression in a host operatively linked to the polynucleotide of the invention to be expressed. Appropriate trans-acting factors are supplied by the host, supplied by a complementing vector or supplied by the vector itself upon introduction into the host.

In certain preferred embodiments in this regard, the expression vectors provide for specific expression. Such specific expression is an inducible expression, cell or organ specific expression, host-specific expression, or a combination thereof.

In one embodiment of the invention, the plant expression vector is an *Agrobacterium*-based expression vector. Various methods are known in the art to accomplish the genetic transformation of plants and plant tissues by the use of *Agrobacterium*-mediated transformation systems, i.e., *A. tumefaciens* and *A. rhizogenesis*. *Agrobacterium* is the etiologic agent of crown gall, a disease of a wide range of dicotyledons and gymnosperms that results in the formation of tumors or galls in plant tissue at the site of infection. *Agrobacterium*, which normally infects the plant at wound sites, carries a large extrachromosomal element called Ti (tumor-inducing) plasmid.

Ti plasmids contain two regions required for tumor induction. One region is the T-DNA (transferred-DNA) which is the DNA sequence that is ultimately found stably transferred to plant genomic DNA. The other region is the vir (virulence) region which has been implicated in the transfer mechanism. Although the vir region is absolutely required for stable transformation, the vir DNA is not actually transferred to the infected plant. Transformation of plant cells mediated by infection with *A. tumefaciens* and subsequent transfer of the T-DNA alone have been well documented. See, i.e., Bevan et al. (1982) Int. Rev. Genet. 16:357, incorporated herein by reference in its entirety.

*A. rhizogenes* has also been used as a vector for plant transformation. This bacterium, which incites root hair formation in many dicotyledonous plant species, carries a large extrachromosomal element called a Ri (root-inducing) plasmid which functions in a manner analogous to the Ti plasmid of *A. tumefaciens*. Transformation using *A. rhizogenes* has developed analogously to that of *A. tumefaciens* and has been successfully utilized to transform the plant of this invention.

*Agrobacterium* systems have been developed to permit routine transformation of a variety of plant tissues. Representative tissues transformed by this technique include, but are not limited to, tobacco, tomato, sunflower, cotton, rapeseed, potato, poplar, and soybean, among others. This technique can be used to modify the other plants listed earlier in this specification having green biomass.

Promoters are responsible for the regulation of the transcription of DNA into mRNA. A number of promoters which function in plant cells are known in the art, and may be employed in the practice of the present invention as described above. These promoters are obtained from a variety of sources such as, for example, plants or plant viruses, bacteria, among others.

The invention, as described and disclosed herein, encompasses the use of constitutive promoters, inducible promoters, or both. In general, an "inducible promoter" is a promoter that is capable of directly or indirectly activating transcription of one or more DNA sequences or genes in response to an inducer such as a chemical (e.g. tetracycline, ethanol or a plant hormone). In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducible promoter can be selected from a chemically-inducible promoter such as a tetracycline-inducible promoter, an ethanol-inducible promoter, and a hormone-inducible promoter.

The inducible promoter can also be selected from a physiologically-inducible promoter such as a heat-inducible promoter, a wound-inducible promoter, a senescence-inducing promoter, and a maturation-inducing promoter.

Inducible promoters are determined using any methods known in the art. For example, the promoter may be operably associated with an assayable marker gene such as GUS (glucouronidase), the host plant can be engineered with the construct; and the ability and activity of the promoter to drive the expression of the marker gene in the harvested tissue under various conditions assayed.

A plant cell containing an inducible promoter is exposed to an inducer by externally applying the inducer to the cell or plant such as by spraying, harvesting, watering, heating or similar methods. In addition, inducible promoters include tissue specific promoters that function in a tissue specific manner to regulate the gene of interest within selected tissues of the plant Examples of such tissue specific promoters include seed, flower or root specific promoters as are well known in the field.

A "constitutive promoter" is a promoter that directs the expression of a gene throughout the various parts of a plant and continuously throughout plant development.

In one embodiment of the invention, promoters are tissue-specific. Non-tissue-specific promoters (i.e., those that express in all tissues after induction), however, are preferred. More preferred are promoters that additionally have no or very low activity in the uninduced state. Most preferred are promoters that additionally have very high activity after induction. Particularly preferred among inducible promoters are those that can be induced to express a protein by environmental factors that are easy to manipulate.

In one embodiment of the invention, one or more constitutive promoters are used to regulate expression of the genes in a plant.

Examples of an inducible and/or constitutive promoters include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), the promoter isolated from the chlorophyll a/b binding protein, proteinase inhibitors (PI-I, PI-II), defense response genes, phytoalexin biosynthesis, phenylpropanoid phytoalexin, phenylalanine ammonia lyase (PAL), 4-coumarate CoA ligase (4CL), chalcone synthase (CHS), chalcone isomerase (CHI), resveratrol (stilbene) synthase, isoflavone reductase (IFR), terpenoid phytoalexins, HMG-CoA reductase (HMG), casbene synthetase, cell wall components, lignin, phenylalanine ammonia lyase, cinnamyl alcohol dehydrogenase (CAD), caffeic acid o-methyltransferase, lignin-forming peroxidase, hydroxyproline-rich glycoproteins (HRGP), glycine-rich proteins (GRP), thionins, hydrolases, lytic enzymes, chitinases (PR-P, PR-Q), class I chitinase, basic, Class I and II chitinase, acidic, class II chitinase, bifunctional lysozyme, β-1,3-Glucanase, *arabidopsis*, β-fructosidase, superoxide dismutase (SOD), lipoxygenase, prot., PR1 family, PR2, PR3, osmotin, PR5, ubiquitin, wound-inducible genes, win1, win2 (hevein-like), wun1, wun2, nos, nopaline synthase, ACC synthase, HMG-CoA reductase hmg1, 3-deoxy-D-arabino-heptulosonate-7-phosphate synthase, HSP7033, Salicylic acid inducible acid peroxidase, PR-proteins, glycine-rich protein, methyl jasmonate inducible, vspB$^{42}$, heat-shock genes, HSP70, cold-stress inducible, drought, salt stress, hormone inducible, gibberellin, α-amylase, abscisic acid, EM-1, RAB, LEA genes, ethylene, phytoalexin biosyn genes, or a combination thereof.

The above-noted promoters are listed solely by way of illustration of the many commercially available and well known plant promoters that are available to those of skill in the art for use in accordance with this aspect of the present invention. It will be appreciated that any other plant promoter suitable for, for example, introduction, maintenance, propagation or expression of a polynucleotide or polypeptide of the invention in plants may be used in this aspect of the invention.

Gene constructs of the present invention can also include other optional regulatory elements that regulate, as well as engender, expression. Generally such regulatory control elements operate by controlling transcription. Examples of such regulatory control elements include, for example, enhancers (either translational or transcriptional enhancers as may be required), repressor binding sites, terminators, leader sequences, and the like.

Specific examples of these elements include, but are not limited to, the enhancer region of the 35S regulatory region, as well as other enhancers obtained from other regulatory regions, and/or the ATG initiation codon and adjacent sequences. The initiation codon must be in phase with the reading frame of the coding sequence to ensure translation of the entire sequence. The translation control signals and initiation codons are from a variety of origins, both natural and synthetic. Translational initiation regions are provided from the source of the transcriptional initiation region, or from the structural gene. The sequence is also derived from the promoter selected to express the gene, and can be specifically modified to increase translation of the mRNA.

The nontranslated leader sequence is derived from any suitable source and is specifically modified to increase the translation of the mRNA. In one embodiment, the 5' nontranslated region is obtained from the promoter selected to express the gene, the native leader sequence of the gene, coding region to be expressed, viral RNAs, suitable eukaryotic genes, or a synthetic gene sequence, among others.

In another embodiment, gene constructs of the present invention comprise a 3U untranslated region. A 3U untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3U end of the mRNA precursor.

The termination region or 3' nontranslated region is employed to cause the termination of transcription and the addition of polyadenylated ribonucleotides to the 3' end of the transcribed mRNA sequence. The termination region may be native with the promoter region, native with the structural gene, or may be derived from the expression vector or another source, and would preferably include a terminator and a sequence coding for polyadenylation. Suitable 3' nontranslated regions of the chimeric plant gene include, but are not limited to: (1) the 3' transcribed, nontranslated regions containing the polyadenylation signal of *Agrobacterium* tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase, among others.

The addition of appropriate introns and/or modifications of coding sequences for increased translation can also substantially improve foreign gene expression. Appropriate introns include, but are not limited to, the maize hsp70 intron, maize adh 1 intron, and rice actin intron.

In one embodiment, the regulatory control elements of the invention include an alfalfa mosaic virus untranslated leader sequence and Lys-Asp-Glu-Leu (KDEL) endoplasmic reticulum retention signal operably attached to the N- and C-terminus of heavy chain, respectively.

It has been shown that the inclusion of KDEL or HDEL amino acid sequences at the carboxy terminus of at least one protein enhanced the recognition for that protein by the plant endoplasmic reticulum retention machinery. See, Munro and Pelham (1987) *Cell* 48:988-997; Denecke et al. (1991) *EMBO-J:* 11:2345; Herman et al. (1991) *Planta* 182:305; and Wandelt et al. (1992) *The Plant Journal* 2:181, each of which is incorporated herein by reference in its entirety.

To aid in identification of transformed plant cells, the gene constructs of this invention may be further manipulated to include selectable marker genes that are functional in bacteria, plants or both. Useful selectable markers include, but are not limited to, enzymes which provide for resistance to an antibiotic such as ampicillin resistance gene ($Amp^r$), tetracycline resistance gene ($Tc^r$), cycloheximide-resistance L41 gene, the gene conferring resistance to antibiotic G418 such as the APT gene derived from a bacterial transposon Tn903, the antibiotic hygromycin B-resistance gene, gentamycin resistance gene, and/or kanamycine resistance gene, among others or herbicides, such as phosphinotricine. Similarly, enzymes providing for production of a compound identifiable by color change such as GUS, or luminescence, such as luciferase, are possible.

A selectable marker gene can be used to select transgenic plant cells of the invention, which transgenic cells have integrated therein one or more copies of the gene construct of the invention. The selectable or screenable genes provide another check for the successful culturing of cells carrying the genes of interest. Transformed plant calli may be selected by growing the cells on a medium containing, for example, kanamycin.

Host plants are genetically transformed to incorporate one or more gene constructs of the invention. There are numerous factors which influence the success of plant transformation. The design and construction of the expression vector influence the integration of the foreign genes into the genome of the host plant and the ability of the foreign genes to be expressed by plant cells. The type of cell into which the gene construct is introduced must, if whole plants are to be recovered, be of a type which is amenable to regeneration, given an appropriate regeneration protocol The integration of the polynucleotides encoding the desired gene into the plant host is achieved through strategies that involve, for example, insertion or replacement methods. These methods involve strategies utilizing, for example, direct terminal repeats, inverted terminal repeats, double expression cassette knock-in, specific gene knock-in, specific gene knock-out, random chemical mutagenesis, random mutagenesis via transposon, and the like. The expression vector is, for example, flanked with homologous sequences of any non-essential plant genes, bacteria genes, transposon sequence, or ribosomal genes. Preferably the flanking sequences are T-DNA terminal repeat sequences. The DNA is then integrated in host by homologous recombination occurred in the flanking sequences using standard techniques.

In one embodiment of the invention, *Agrobacterium*-based transformation strategy is employed to introduce the gene constructs into plants. Such transformations preferably use binary *Agrobacterium* T-DNA vectors (Bevan (1984) supra), and the co-cultivation procedure (Horsch et al. (1985) Science 227:1229-1231, incorporated herein by reference in its entirety). Generally, the *Agrobacterium* transformation system is used to engineer dicotyledonous plants. The *Agrobacterium* transformation system may also be used to transform as well as transfer DNA to monocotyledonous plants and plant cells. See, for example, Hernalsteen et al. (1984) EMBO J. 3:3039-3041; Hooykass-Van Slogteren et al. (1984) Nature 311:763-764; Grimsley et al. (1987) Nature 325:1677-179; Boulton et al. (1989) Plant Mol. Biol. 12:3140; Gould et al. (1991) Plant Physiol. 95:426-434, each of which is incorporated herein by reference in its entirety.

In other embodiments, various alternative methods for introducing recombinant nucleic acid constructs into plants and plant cells are also utilized. These other methods are particularly useful where the target is a monocotyledonous plant or plant cell. Alternative gene transfer and transformation methods include, but are not limited to, protoplast transformation through calcium-polyethylene glycol (PEG)- or electroporation-mediated uptake of naked DNA. See, for example, Paszkowski et al. (1984) EMBO J. 3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276, each of which is incorporated herein by reference in its entirety. Electroporation of plant tissues are also disclosed in D'Halluin et al. (1992) Plant Cell 4:1495-1505, incorporated herein by reference in its entirety. Additional methods for plant cell transformation include microinjection, silicon carbide mediated DNA uptake (see, for example, Kaeppler et al. (1990) Plant Cell Reporter 9:415418), and microprojectile bombardment (see, for example, Klein et al. (1988) Proc. Nat. Acad. Sci. USA 85:4305-4309; Gordon-Kamm et al. (1990) Plant Cell 2:603-618, each of which is incorporated herein by reference in its entirety In the case of direct gene transfer, the gene construct is transformed into plant tissue without the use of the *Agrobacterium* plasmids. Direct transformation involves the uptake of exogenous genetic material into plant cells or protoplasts. Such uptake may be enhanced by use of chemical agents or electric fields. The exogenous material may then be integrated into the nuclear genome.

The early work with direct transfer was conducted in the *Nicotiana tobacum* (tobacco) where it was shown that the foreign DNA was incorporated and transmitted to progeny plants. Several monocot protoplasts have also been transformed by this procedure including maize and rice.

Liposome fusion has also been shown to be a method for transforming plant cells. Protoplasts are brought together with liposomes carrying the desired gene. As membranes merge, the foreign gene is transferred to the protoplasts.

Alternatively, exogenous DNA can be introduced into cells or protoplasts by microinjection. In this technique, a solution of the plasmid DNA or DNA fragment is injected directly into the cell with a finely pulled glass needle.

A more recently developed procedure for direct gene transfer involves bombardment of cells by micro-projectiles carrying DNA. In this procedure, commonly called particle bombardment, tungsten or gold particles coated with the exogenous DNA are accelerated toward the target cells. The particles penetrate the cells carrying with them the coated DNA. Microparticle acceleration has been successfully demonstrated to lead to both transient expression and stable expression in cells suspended in cultures, protoplasts, immature embryos of plants including but not limited to onion, maize, soybean, and tobacco.

In addition to the methods described above, a large number of methods are known in the art for transferring cloned DNA into a wide variety of plant species, including gymnosperms, angiosperms, monocots and dicots. Minor variations make these technologies applicable to a broad range of plant species.

The invention further relates to transgenic plants, including whole plants, plant organs (i.e., leaves, stems, flowers, roots, etc.), seeds and plant cells (including tissue culture cells), and progeny of same that are transformed with a gene construct according to this invention.

Once plant cells have been transformed, there are a variety of methods for regenerating plants. The particular method of regeneration will depend on the starting plant tissue and the particular plant species to be regenerated. In general, transformed plant cells are cultured in an appropriate medium, which contain selective agents such as, for example, antibiotics, where selectable markers are used to facilitate identification of transformed plant cells. Once callus forms, embryo or shoot formation are encouraged by employing the appropriate plant hormones in accordance with known methods, and the shoots transferred to rooting medium for regeneration of plants. The plants are then used to establish repetitive generations, either from seeds or using vegetative propagation techniques. The presence of a desired gene, or gene product, in the transformed plant may be determined by any suitable method known to those skilled in the art. Included in these methods are southern, northern, and western blot techniques, ELISA, and bioassays.

In recent years, it has become possible to regenerate many species of plants from callus tissue derived from plant explants. The plants which can be regenerated from callus include monocots, such as, but not limited to, corn, rice, barley, wheat, and rye, and dicots, such as, but not limited to, sunflower, soybean, cotton, rapeseed and tobacco.

It will be appreciated that polypeptides often contain amino acids other than the 20 amino acids commonly referred to as the "naturally occurring" amino acids, and that many amino acids, including the terminal amino acids, may be modified in a given polypeptide, either by natural processes, such as processing and other post-translational modifications, or by chemical modification techniques.

Modifications can occur anywhere in a polypeptide, including the peptide backbone, the amino acid side chains and the amino or carboxyl termini. Blockage of the amino or carboxyl group in a polypeptide, or both, by a covalent modification, occur in natural or synthetic polypeptides. Such modifications may be present in the polypeptides of the present invention, as well. In general, the nature and extent of the modifications are determined by the host cell's post-translational modification capacity and the modification signals present in the polypeptide amino acid sequence. It will be appreciated that the same type of modification may be present in the same or varying degrees at several sites in a polypeptide.

Variations in the structure of the polypeptides may arise naturally as allelic variations, as disclosed above, due to genetic polymorphism, for example, or may be produced by human intervention (i.e., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules.

Substitutions may be designed based on, for example, the model of Dayhoff et al. (1978) Atlas of Protein Sequence and Structure, Natl. Biomed. Res. Found. Washington, D.C. These modifications can result in changes in the amino acid sequence, provide silent mutations, modify a restriction site, or provide other specific mutations.

This invention also encompasses plants comprising polynucleotides that correspond to and code for the genes of the present invention. Nucleic acid sequences are either synthesized using automated systems well known in the art, or derived from a gene bank.

It will be appreciated that a great variety of modifications have been made to DNA and RNA that serve many useful purposes known to those of skill in the art. The polynucleotides of the invention embrace chemically, enzymatically or metabolically modified forms of polynucleotides.

The polynucleotides of the present invention encode, for example, the coding sequence for the structural gene, and additional coding or non-coding sequences. Examples of additional coding sequences include, but are not limited to, sequences encoding a secretory sequence, such as a pre-, pro-, or prepro-protein sequences. Examples of additional non-coding sequences include, but are not limited to, introns and non-coding 5' and 3' sequences, such as the transcribed, non-translated sequences that play a role in transcription and mRNA processing, including splicing and polyadenylation signals, for example, for ribosome binding and stability of mRNA.

The polynucleotides of the invention also encode a polypeptide which is the mature protein plus additional amino or carboxyl-terminal amino acids, or amino acids interior to the mature polypeptide (when the mature form has more than one polypeptide chain, for instance). Such sequences play a role in, for example, processing of a protein from precursor to a mature form, may facilitating protein trafficking, prolonging or shortening protein half-life or facilitating manipulation of a protein for assay or production, among others. The additional amino acids may be processed away from the mature protein by cellular enzymes.

In sum, the polynucleotides of the present invention encodes, for example, a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

The polynucleotides of the invention include "variant(s)" of polynucleotides, or polypeptides as the term is used herein. Variants include polynucleotides that differ in nucleotide sequence from another reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference.

Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence. According to one embodiment of the invention, there are no alterations in the amino acid sequence of the polypeptide encoded by the polynucleotides of the invention, as compared with the amino acid sequence of the wild type or mammalian derived peptide.

The present invention further relates to polynucleotides that hybridize to the herein described sequences. The term "hybridization under stringent conditions" according to the present invention is used as described by Sambrook et al. (1989) Molecular Cloning, A Laboratory Manual, Cold Spring Harbor Laboratory Press 1.101-1.104. Preferably, a stringent hybridization according to the present invention is given when after washing for an hour with 1% SSC and 0.1% SDC at 50° C., preferably at 55° C., more preferably at 62° C., most preferably at 68° C. a positive hybridization signal is still observed. A polynucleotide sequence which hybridizes under such washing conditions with the nucleotide sequence shown in any sequence disclosed herein or with a nucleotide sequence corresponding thereto within the degeneration of the genetic code is a nucleotide sequence according to the invention.

The polynucleotides of the invention include polynucleotide sequences that have at least about 50%, 65%, 70%, 75%, 80%, 85%, 90%, 95%, 98%, 99% or more nucleotide sequence identity to the polynucleotides or a transcriptionally active fragment thereof. To determine the percent identity of two amino acid sequences or two nucleic acid sequences, the sequences are aligned for optimal comparison purposes (i.e., gaps can be introduced in the sequence of a first amino acid or nucleic acid sequence for optimal alignment with a second nucleic acid sequence). The amino acid residue or nucleotides at corresponding amino acid or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100). In one embodiment, the two sequences are the same length.

The determination of percent identity between two sequences also can be accomplished using a mathematical algorithm. One, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST program of Altschul et al. (1990), J. Mol. Biol. 215:403-410. BLAST nucleotide searches can be performed with the NBLAST program, score=100, wordlength=12 to obtain nucleotide sequences homologous to a nucleic acid molecules of the invention. The BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al. (1997) Nucleic Acids Res. 25:3389-3402.

Alternatively, PSI-Blast can be used to perform an iterated search which detects distant relationships between molecules (Id.). When utilizing BLAST, Gapped BLAST and PSI-Blast programs, the default parameters of the respective programs (i.e., XBLAST and NBLAST program can be used (see, HTrP://WWW.NCBI.NLM.NIH.GOV). Another preferred, non-limiting example of a mathematical algorithm utilized for the comparison of sequences is the algorithm of Myers and Miller (1988) CABIOS 4:11-17. Such an algorithm is incorporated into the ALIGN program (version 2.0) which is part of the GCG sequence alignment software package. When utilizing the ALIGN program for comparing amino acid sequences of a PAM 120 weight residue table, a gap length penalty of 12 and a gap penalty of 4 can be used. In an alternate embodiment, alignments can be obtained using the NA-MULTIPLE-ALIGNMENT 1.0 program, using a Gap Weight of 5 and a GapLengthWeight of 1.

This invention is further illustrated by the following examples, which are not to be construed in any way as imposing limitations upon the scope of the invention.

EXAMPLES

Example 1

Construction of Plant Transformation Binary Vector cDNA fragments encoding for acyl CoA:diacylglycerol acyltransferase from *Arabidopsis thaliana* (AtDGAT; GeneBank Accession #BT008883; SEQ ID NO:1) are arranged into a pBI121-derived binary vector (Clonetech, Palo Alto, Calif.) as follows. AtDGAT is amplified via PCR with primers containing NcoI and NotI sites (5'-gAA ACC ATg gCg ATT TTg gAT TCT gC-3'(SEQ ID NO: 2) and: 5'-ATC TgC ggC CgC TgA CAT CgA TCC TTT TCg gT-3' (SEQ ID NO: 3), and is cloned in multiple cloning site of an intermediate Impact Vector pIV1.1tag under the control of Rubisco (rbcS) strong promoter with rbcS terminator. The resulting construct was confirmed by DNA-sequencing. The whole cassette was then subcloned in pBI-derived pBIN-PLUS binary vector. In another version the coding region of same AtDGAT gene was cut from intermediate vector using NcoI-NotI restriction enzymes and cloned in pBI121 vector under the cauliflower mosaic virus (CaMV) 35S strong promoter with duplicated upstream B domains (Ca2p) (Kay et al. (1987) Science 236:1299-1302). In another version the original Kanamycin-resistance plant-selection marker in this resulting construct was replaced with a herbicide phosphinotricin (PPT)-resistance selection marker by cutting kanamycin-resistance gene with the restriction enzymes NheI-AscI and replacing it for PCR-amplified synthetic PPT-acetyltransferase (PAT1) gene [NCBI Accession Number A02774, modified by generation of NheI and AscI restriction sites, correspondingly cDNA fragments encoding for LEC2 (GeneBank Accession #DQ446296; SEQ ID NO: 4) are arranged into a plant transformation vector pNB-Alc-B3 as follows. LEC2 is amplified via PCR with primers containing BglII sites (5'-tagatctgccatggataacttcttaccctttccc (SEQ ID NO: 5) and 5'-TAGATCTTCACCACCACTCAAAGTCGTTAAAGCTC-ACC (SEQ ID NO: 6)), and is cloned into BamHI site of the plasmid pACN under the control of the ethanol-inducible promoter AlcA isolated from fungus *Aspergillus nidulans* (Felenbok B. The ethanol utilization regulon of *Aspergillus nidulans*: the alcA-alcR system as a tool for expression of recombinant proteins. J. Biotechnol., 1991, 17: 11-18) and nos-terminator. The expression cassette is then cut out by partial digestion with HindIII and cloned into HindIII site of pBinAlc under the control of ethanol regulator alcR, resulting in ethanol regulated vector pNB-Alc-B3.

Example 2

Plant Transformation

Tobacco leaf explants (*Nicotiana tabacum* cv. Wisconsin) are used for *Agrobacterium*-mediated transformation (*A. tumefaciens* EHA105) in MS-based media (Hiatt et al. (1989) Nature 342:76-78) according to the described protocols (Ko et al. (2000) supra). Tobacco transgenic lines are generated by *Agrobacterium*-mediated plant transformation with a vector carrying DGAT. Independent transgenic lines were selected on kanamycin (100 µg/ml). Transgenic tobacco lines were later maintained in soil, and subsequent generations (T1 and T2) were obtained by self-fertilization.

Tobacco leaf explants (*Nicotiana tabacum* cv. Wisconsin) are used for *Agrobacterium*-mediated transformation (*A. tumefaciens* EHA105) in MS-based media (Hiatt et al. (1989) Nature 342:76-78) according to the described protocols (Ko et al. (2000) supra). Tobacco transgenic lines are generated by *Agrobacterium*-mediated plant transformation with a vector carrying LEC2. Independent transgenic lines were selected on kanamycin (100 µg/ml). Transgenic tobacco lines were later maintained in soil, and subsequent generations (T1 and T2) were obtained by self-fertilization.

The transgenic plants constitutively expressing DGAT are then genetically crossed with the transgenic plants inducibly expressing LEC2 in order to generate a transgenic plant comprising both genes.

Example 3

Molecular Characterization of Transgenic Plants

PCR amplification of both DGAT and LEC2 is performed with genomic DNA of each transgenic line using the same primers as described above. Protein expression analysis of both DGAT and LEC2 was confirmed by western blot.

Example 4

SDS-PAGE and Protein Blot Analysis

One gram of tobacco leaf tissues is ground in liquid nitrogen with 100 µl of extraction buffer (50 mM Tris, pH 7.5, 250 mM sucrose) containing protease "complete" inhibitor cocktail (Roche, Indianapolis, Ind.). Forty µg of soluble protein (in 10 µl) is resolved by 12% SDS-PAGE and transferred to Immobilon-P Transfer Membrane (Millipore Corp., Bedford, Ma.) using a mini-Protean II™ system (Bio-Rad Labs, Hercules, Calif.) according to the manufacturer's recommendations. Anti-DGAT and anti-LEC2 antibodies are applied to detect DGAT and LEC2. The signal is detected using incubation with a HRP-conjugated secondary antibody followed by treatment with "SuperSignal" chemiluminescence substrate (Pierce, Rockford, Ill.).

Example 5

Detection and Measurement of Oil Production

In order to estimate the effect of DGAT on fatty acid biosynthesis in tobacco, we carried out two types of analyses. First, the triacylglyceride (TAG) fraction of tobacco biomass was examined using LC-MS that allows not only quantification of TAG in transgenic lines relative to that in wild-type tobacco, but also determination of the composition of TAG in individual plants. Second, total fatty acid esters, which constitute the biofuel oil used in diesel engines, were quantified by gas chromatography (GC) following the esterification of extracted fatty acids with acidic methanol (Rogozinski, 1964). For both tests, fatty acids were isolated from 100 mg of freeze-dried samples collected from 3-month-old plants, using either modified hexane extraction or classic chloroform-methanol isolation (Bligh, Dyer 1959).

Figure 4:
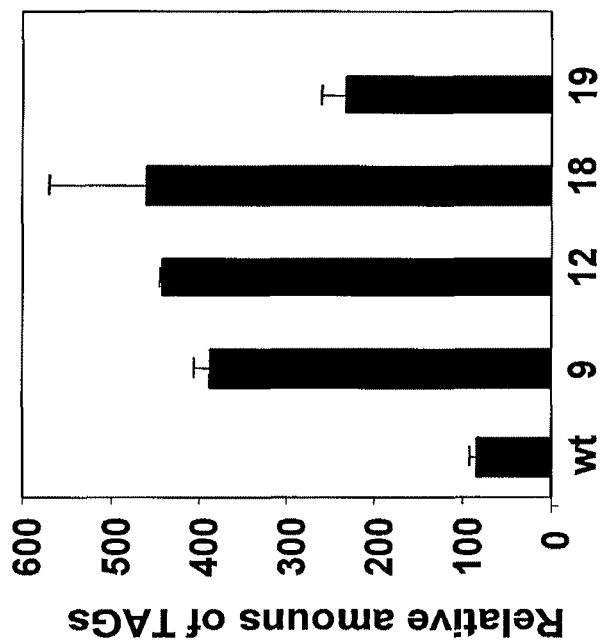
FIG. 4. is a graph representing the relative amounts of triacylglycerols ("TAGs") as determined by liquid chromatography (LC-MS) in wt—wild type tobacco, *Nicotiana tabacum*, cv Wisconsin; as compared to selected genetically modified plants of this invention (nos. 9, 12, 18 and 19) that over-express DGAT.

LC-MS analysis revealed a 3- to 7-fold increase in TAG accumulation in leaves of tobacco plants 9, 12, 18, and 19 (FIG. 4) overexpressing DGAT compared with the unmodified counterpart tobacco plant ("wt).

As shown in FIGS. 6 A and B, quantitative gas chromatography (GC) analysis of fatty acids indicated an overall 100-150% increase in extracted fatty acid esters in modified tobacco plants 1-15 compared with the unmodified counterpart ("wt") (FIG. 6A)

Figure 5:
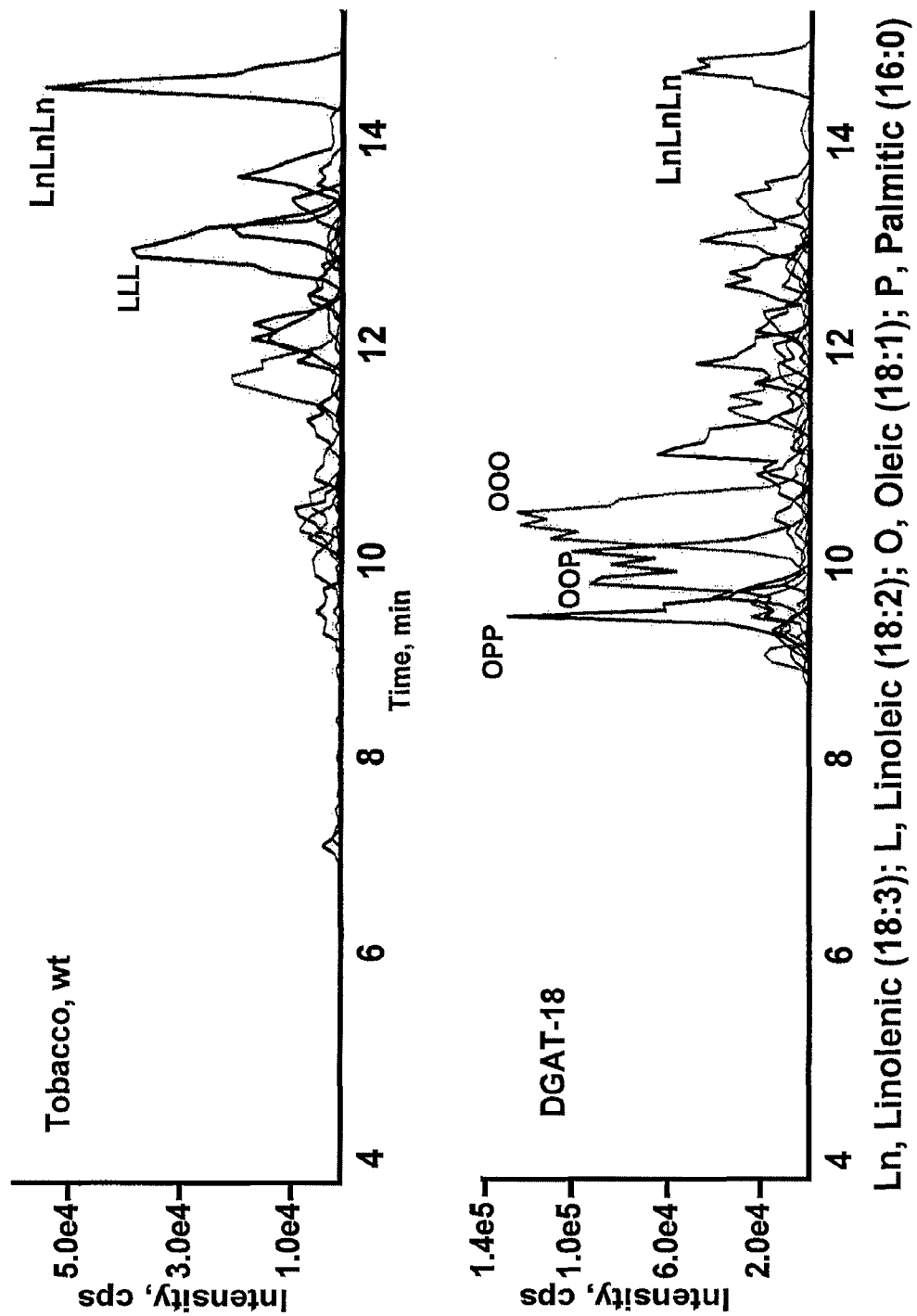
FIG. 5 is a chromatogram showing composition of various types of TAGs in green biomass of non-modified (top) and modified tobacco (bottom).

This increase in total fatty acid accumulation in tobacco leaves was accompanied by a significant shift in the fatty acid composition (see FIGS. 5 and 6B). Three fatty acids, linolenate (18:3), linoleate (18:2) and palmitate (16:0), are usually predominant in plant biomass, as also seen in tobacco (Koiwai et al., 1983). In different transgenic tobacco lines of this invention (1-15; FIG. 6B), the proportion of linolenate was reduced to 30-40% as compared to 50-60% in wild-type plants, while oleate (18:1) increased from 1.5% to 20-25% in total extracted fatty acids (see FIG. 6B) compared with the unmodified counterpart plant ("wt").

The changes in the TAG fraction of tobacco oil in DGAT-overexpressing tobacco were even more profound, with a substantial decrease in both 3-linolenate (LnLnLn) and 3-linoleic (LLL) and an increase of oleic acid containing TAGs (i.e., OOO, OOP and OPP) (FIG. 5 bottom).

In the context of developing tobacco biomass oil into a diesel fuel, such a shift (FIG. 5B; FIG. 6) is definitely desirable. First, it makes tobacco biomass oil composition more similar to canola oil, which contains about 60% oleate and which has been exploited as a standard biodiesel fuel in Europe for more than 20 years. Second and perhaps more important is the reduction in heavily unsaturated linolenate (18:3), whose concentration in plant-derived oil is subject to biodiesel standards regulation in some countries.

Using the DGAT-overexpressing plants produced in Stage 1, we can further augment oil accumulation through controlled expression of the gene LEC2, a master regulator of seed maturation and seed oil storage, and shown to trigger oil accumulation when expressed in leaves. Expression of the LEC2 gene under the control of the well-characterized ethanol-inducible promoter AlcA isolated from *Aspergillus nidulans* can be stimulated just before harvest, when tobacco biomass is optimal, by watering plants with a 0.1% ethanol solution. This will activate seed-specific genes within the leaves to further accelerate oil biosynthesis and generate seed-specific structures for oil accumulation and storage. This modification can increase oil accumulation in tobacco biomass to 5-8% of dry weight, yielding more oil per acre than soybean (see Table 2).

TABLE 2

Theoretical yields of biofuel oil from soybean and tobacco.

| Feedstock | Gallons/ton of dry weight | Gallons/acre |
| --- | --- | --- |
| Soybean Grain | 55.6 | 64 |
| Tobacco Biomass | 14 | 140 |

Based on 2004 USA soybean yield of 1.15 tons/acre, tobacco biomass of 100 tons/acre, and oil accumulation at 5% of dry tobacco biomass.

The left-over plant matter, including the green biomass following oil extraction can be used to make ethanol using fermentation techniques. Generating both ethanol and biofuel oil, tobacco modified according to this invention has the potential to produce more energy per acre than any other American crop. Since tobacco is a non-food plant that can thrive in poor soil, it does not compete with food-producing plants such as corn and soybeans for more fertile soil.

While tobacco (*Nicotiana tabacum* and other species from the *Nicotiana* genus) is the subject of examples above, other plants can be modified according to the teachings of this invention with the same technology based on their high biomass production and/or ability to accumulate oil, as discussed below.

Sunflower is one of the staple crops used for production of vegetable seed oil. Unlike other oil producing crops such as soybean and rape-seed, sunflower, due to its big size, can also generate a substantial amount of green biomass. Similar to tobacco, sunflower possesses a potent seed oil biosynthesis pathway that can be modified and relocated to green biomass using the genetic modification techniques of this invention described above using the same kinds of gene modifications. At least two protocols for *Agrobacterium*-mediated transformation of sunflower have been developed that can be also be used to modify sunflower to include the novel genetic modifications consistent with this invention: (1) Weber S, Friedt W, Landes N, Molinier J, Himber C, Rousselin P, Hahne G, Horn R. Improved *Agrobacterium*-mediated transformation of sunflower (*Helianthus annuus* L.): assessment of macerating enzymes and sonication. Plant Cell Rep. 2003 January; 21(5):475-82. 2; and (2) Müller A, Iser M, Hess D., Stable transformation of sunflower (*Helianthus annuus* L.) using a non-meristematic regeneration protocol and green fluorescent protein as a vital marker. Transgenic Res. 2001 October; 10(5):435-44.

Industrial hemp is a another plant that can be modified consistent with the teaching of this invention. It can be grown in many areas of the world. In Europe and Canada it has traditionally been utilized as energy source plant. For example, *Cannabis sativa*, commonly know as "hemp" is included in a list of potential field crops considered as Candidate Energy Crops in the December 1999 California Energy Commission report "Evaluation Of Biomass-To-Ethanol Fuel Potential In California" pg. iv-3]. Genetic transformation of hemp consistent with the teachings of this invention can be performed via *Agrobacterium* [Feeney M., Punja Z. K. Hemp (*Cannabis sativa* L.). In: Methods Mol Biol 2006; 344:373-82].

Corn is another plant that can be transformed consistent with the teachings of this invention. Extracting of oil accumulated in corn green biomass from corn plants modified according to this invention can improve efficiency of oil production. Methods for enetic transformation of corn are well established (Ishida Y, Hiei Y, Komari T. *Agrobacterium*-mediated transformation of maize. Nat Protoc. 2007; 2(7):1614-1621). These same methods can be employed to make the novel genetic modifications of this invention.

Switchgrass is another plant that can be modified to incorporate the novel genetic modifications of this invention. Unmodified switchgrass is a leading energy plant candidate under consideration by United States Department of Energy. Numerous studies are known to use switchgrass for ethanol production, however both oil end ethanol utilization is possible after improving oil content in switchgrass using the methods of this invention. Transformation via *Agrobacterium* is also available [Somleva M. N. Switchgrass (*Panicum virgatum* L.). In: Methods Mol Biol. 2006; 344:65-73].

Duck weed (*Lemna* sp.) Aquatic plant *Lemna* has unique, innate characteristics that provide enormous value for biomass production so that it can be modified to include the novel genetic modifications of this invention. The advantages include: versatility, fast and flexible operation, low capital costs for facilities, low operating costs, and environmental safety. As a green plant it has similar pathways of oil production, and its oil content can be improved with the techniques of this invention. *Agrobacterium*-mediated transformation of *Lemna* was developed [Yamamoto Y. T. et al. Genetic transformation of duckweed *Lemna gibba* and *Lemna minor*. In Vitro Cell Dev. Biol. Plant 2001; 37:349-353].

Sugarcane, sorghum, and sugar beet are already used as a source for bioethanol; Hill. J., et al. Environmental, economic, and energetic costs and benefits of biodiesel and ethanol biofuels. Proc. Natl. Acad. Sci. USA, 2006, 103: 11206-11210], however genetically modifying these plants to incorporate the novel genetic modifications of this invention to increase oil in the green biomass of these plants can increase total energy efficiency. Oil production from sugarcane, sorghum and sugar beet could be economically feasible after their genetic modification based on proposed invention. Genetic transformation is described for sugarcane [Shrawat A. K., Lorz H. *Agrobacterium*-mediated transformation of cereals: a promising approach crossing barriers. Plant Biotechnol J. 2006, 4(6): 575-603. Review] and sugar beet [Golovko A. E., Dovzhenko A. A., Gleba Yu. Yu. Genetic transformation of sugar beet: evolution of theoretical and experimental approaches. Tsitol Genet. 2005, 39(3): 30-6. Review.]. Several techniques for genetic transformation of sorghum have been established (Casas A M, Kononowicz A K, Zehr U B, Tomes D T, Axtell J D, Butler L G, Bressan R A, Hasegawa P M. Transgenic sorghum plants via microprojectile bombardment. Proc Natl Acad Sci USA. 1993 Dec. 1; 90(23):11212-6.2: Zhao Z Y, Cai T, Tagliani L, Miller M, Wang N, Pang H, Rudert M, Schroeder S, Hondred D, Seltzer J, Pierce D. *Agrobacterium*-mediated sorghum transformation. Plant Mol Biol. 2000 December; 44(6):789-98. 3: Gao Z, Xie X, Ling Y, Muthukrishnan S, Liang G H. *Agrobacterium* tumefaciens-mediated sorghum transformation using a mannose selection system. Plant Biotechnol J. 2005 November; 3(6):591-9.)

The present invention may be embodied in other specific methods, products, and forms without departing from its spirit of essential characteristics. The embodiments and examples provided in this specification are intended to illustrate the principles of the invention, but not to limit its scope. Various other embodiments, examples, modifications, and equivalents to the embodiments and examples provided in this specification may occur to those skilled in the art upon reading the present disclosure or practicing the present invention. Such variations, modifications, examples, and equivalents are intended to come within the scope of the invention. The contents of all references, patents and published patent applications cited throughout this application are expressly incorporated herein by reference.

We claim:

1. A genetically modified tobacco plant having an increased amount of oil as compared to a non-genetically modified tobacco plant, wherein said genetically modified tobacco plant is genetically modified to stimulate increased oil accumulation in green biomass as compared to its non-genetically modified counterpart, wherein said genetically modified tobacco plant has increased expression of:
   a first transgene that encodes an AtDGAT1 polypeptide that is operably linked to a constitutive promoter; and
   a second transgene that encodes an *Arabidopsis* LEC2 transcription factor that is operably linked to an inducible promoter.

2. The genetically modified plant according to claim 1, wherein said first transgene encodes a polypeptide comprising diacylglycerol acyltransferase SEQ ID NO: 7.

3. The genetically modified plant according to claim 1, wherein said *Arabidopsis* LEC2 transcription factor is operably linked to an ethanol inducible promoter.

4. The genetically modified plant according to claim 1, wherein said first transgene encodes an AtDGAT1 polypeptide and is operably linked to a Rubisco promoter.

5. A process for making a biofuel, comprising:
   extracting oil from at least the green biomass of a genetically modified tobacco plant having an increased amount of oil in its green biomass as compared to the green biomass of its non-genetically modified counterpart, wherein said genetically modified tobacco plant has increased expression of:
   a first transgene that encodes an AtDGAT1 polypeptide and is operably linked to a constitutive promoter or an inducible promoter, and
   a second transgene that encodes an *Arabidopsis* LEC2 transcription factor and is operably linked to an inducible promoter; and
   subjecting the extracted oil to a transesterification process to produce said biofuel.

6. The process of claim 5, wherein said first transgene encodes a polypeptide comprising diacylglycerol acyltransferase SEQ ID NO: 7.

7. The process of claim 5, wherein said first transgene encodes an AtDGAT1 polypeptide and is operably linked to a Rubisco promoter.

8. The process of claim 5, wherein said second transgene encodes an *Arabidopsis* LEC2 transcription factor and is operably linked to an ethanol inducible promoter.

9. The process of claim 5, wherein said first transgene encodes an AtDGAT1 polypeptide and is operably linked to a CaMV35S promoter.

10. A genetically modified tobacco plant having an increased amount of oil as compared to a non-genetically modified tobacco plant, wherein said genetically modified tobacco plant is genetically modified to stimulate increased oil accumulation in green biomass as compared to its non-genetically modified counterpart, wherein said genetically modified tobacco plant has increased expression of:
   a first transgene that encodes an AtDGAT1 polypeptide and is operably linked to an inducible promoter; and
   a second transgene that encodes an *Arabidopsis* LEC2 transcription factor and is operably linked to an inducible promoter.

11. The genetically modified plant according to claim 10, wherein said first transgene encodes a polypeptide comprising diacylglycerol acyltransferase SEQ ID NO: 7.

12. The genetically modified plant according to claim 10, wherein said second transgene encodes an *Arabidopsis* LEC2 transcription factor and is operably linked to an ethanol inducible promoter.

* * * * *